(12) United States Patent
Bansal et al.

(10) Patent No.: US 8,506,717 B2
(45) Date of Patent: Aug. 13, 2013

(54) METHODS OF TREATING A BIOMASS FOR ENZYMATIC HYDROLYSIS

(75) Inventors: Prabuddha Bansal, Atlanta, GA (US); Andreas Sebatian Bommarius, Atlanta, GA (US); Melanie Hall, Graz (AT); Jay Hyung Lee, Daejeon (KR)

(73) Assignee: Georgia Tech Research Corporation, Atlanta, GA (US)

( * ) Notice: Subject to any disclaimer, the term of this patent is extended or adjusted under 35 U.S.C. 154(b) by 50 days.

(21) Appl. No.: 12/960,241

(22) Filed: Dec. 3, 2010

(65) Prior Publication Data
US 2011/0247609 A1 Oct. 13, 2011

Related U.S. Application Data

(60) Provisional application No. 61/266,618, filed on Dec. 4, 2009.

(51) Int. Cl.
*C13K 1/02* (2006.01)

(52) U.S. Cl.
USPC .......................................................... 127/37

(58) Field of Classification Search
None
See application file for complete search history.

(56) References Cited

U.S. PATENT DOCUMENTS

| | | |
|---|---|---|
| 2008/0299613 A1 | 12/2008 | Merino et al. |
| 2009/0042266 A1 | 2/2009 | Vehmaanpera et al. |

OTHER PUBLICATIONS

Jeoh et al, cellulase digestability of pretreated biomass is limited by cellulose accessibility, 2007, biotechnology and bioenigeering, vol. 98, No. 1.*

Zhou et al, optmization of cellulase mixture for efficient hydrolysis of steam exploded corn stover by statistically desgined experiments, 2008, bioresource techonolgy. pp. 819-825.*

Lemos et al., "The Enhancement of the Celluloytic Activity of Cellobiohydrolase I and Endogulcanase by the Addition of Cellulose Binding Domains Derived from Trichoderma Reesei", Enzyme and Microbial Technology, vol. 32 (2003), pp. 35-40.

Levy et al., "Cellulose-Binding Domains Biotechnological Applications", Biotechnology Advances, vol. 20 (2002), pp. 191-213.

Medve et al., "Hydrolysis of Microcrystalline Cellulose by Cellobiohydrolase I and Engoglucanase II from *Trishoderma reesei*: Absorption, Sugar Production Pattern and Synergisum of the Enzymes", Biotechnology and Bioengineering, Sep. 5, 1998, vol. 59, No. 5, pp. 621-634.

Srisodsuk et al., "*Trichoderm reesei* Cellobiohydrolase I with an Endoglucanase Cellulose-Binding Domain: Action on Bacterial Microcrystalline Cellulose", Journal of Biotechnology, vol. 57 (1997), pp. 49-57.

Szengyel et al., "Cellulase Production of *Trichoderma reesei* Rut C 30 Using Steam-Preteated Spruce: Hydrolytic Potential of Cellulases on Different Substrates", Applied Biochemistry and Biotechnology, vol. 84-86 (2000), pp. 679-691.

PCT/US10/58960, filed Dec. 3, 2010, Notification of Transmittal of the International Search Report and the Written Opinion of the International Searching Authority dated Mar. 28, 2011, 8 pages.

* cited by examiner

*Primary Examiner* — Melvin C Mayes
*Assistant Examiner* — Stefanie Cohen

(57) ABSTRACT

The present invention is a process for treating a feedstock comprising holocellulose. The process comprises mixing the feedstock with a solution comprising cellulose binding domains to form a mixture. The mixture is then subjected to conditions sufficient to reduce the crystallinity of holocellulose. Subsequent enzymatic hydrolysis may show an improved rate and/or fermentable sugar yield as compared to processes which do not employ the process.

24 Claims, 13 Drawing Sheets

FIG. 19

```
                          10         20         30
                          |          |          |
7|7/1-36         TQTHYGQCGGTGWTGPTRCASCFTCQVLNPFYSQCL
11|11/1-36       TQTHYGQCGGQGWTGPTACASFYTCQVLNPWYSQCL
29|29/1-36       TVPKYGQCGGQGWSGPTTCASGSTCQALNDFYSQCV
43|43/1-33       ---HYGQCGGNGWQGPTTCASFYTCQKLNDFYSQCL
19|19/1-36       TQTHWGQCGGQGWTGPTQCESGTTCQVISQWYSQCL
28|28/1-35       -QVKYGQCGGSGWTGPTLCESCSTCQVQNQWYSQCL
39|39/1-35       -QSLYGQCGGNGWSGPTECTACACCQVQNPWYSQCL
41|41/1-34       --SQWGQCGGQGWSGPTCCPSCTTCQLQNAWYSQCL
1|1/1-36         TQSHYGQCGGIGYSGPTVCASCTTCQVPYYSQCL
2|2/1-36         TQSHYGQCGGIGYSGPTVCASCTTCQVLNPYYSQCL
5|5/1-33         ---HYGQCGGIGYSGPTVCASCTTCQVLNPYYSQCL
3|3/1-36         TQTHYGQCGGIGYSGPTVCASCTTCQVLNEYYSQCL
4|4/1-36         TQTHYGQCGGIGYSGPTVCASCTTCQVLNEYYSQCL
6|6/1-36         TQTHYGQCGGIGYSGPTQCVSCTTCQVLNPFYSQCL
10|10/1-33       ---HWGQCGGIGWSGPTICVSPYTCQVLNPYYSQCL
20|20/1-35       TAAQWAQCGGMGFTGPTVCASPFTCHVLNPYYSQC-
30|30/1-35       TVAQWGQCGGTGFTGPTVCASPFTCHVVNPYYSQC-
15|15/1-31       ----WGQCGGIGYTGPTVCASCFTCHVLNPYYSQC-
16|16/1-30       ------GQCGGIGYTGPTTCASPTTCHVLNPYYSQC-
9|9/1-34         --SEWGQCGGIGWTGPTTCVSGTTCTVLNPYYSQCL
31|31/1-33       ---EWGQCGGIGWTGPTTCVACTTCVESNPYYSQCL
12|12/1-34       --AHWGQCGGQGWTGPTTCASCTTCTVVNPYYSQCL
13|13/1-33       ---HWGQCGGQGWTGPTTCVSGTTCTVVNPYYSQCL
32|32/1-32       ----WGQCGGQGYTGPTACVSGTTCKAQNPYYSQCL
33|33/1-32       ----WGQCGGQGYTGPTACVSGTTCKAQNPYYSQCL
17|17/1-33       ---KWGQCGGIGWTGPTTCVSGTTCQKLNDWYSQCL
38|38/1-34       --AKYGQCGGLTYTGPTTCVSGTTCTALNDYYSQCL
23|23/1-33       ---HWAQCGGVGYSGPTACASPYTCKVQNDYYSQCL
37|37/1-36       TADHWAQCGGRGFSGPTTCASCAVCTVVNEWYSQCL
34|34/1-32       -----WGQCGGLGWTGPTVCASCFTCTVINEYYSQCL
36|36/1-34       --EHWGQCGGNGWTGPTACASGYTCTVINEWYSQCL
35|35/1-32       -----YGQCGGIGWTGATTCVSGATCTVLNPYYSQCL
44|44/1-32       -----YGQCGGIGWSGATTCVSCATCTVVNAYYSQCL
14|14/1-36       TQTLYGQCGGSGWTGPTACASGATCKVLNSYYSQCL
8|8/1-36         TQTKYGQCGGQGYSGPTVCASGSTCQTSNPYYSQCL
40|40/1-36       TQTKYGQCGGQGWTGATVCASGSTCTSSGPYYSQCL
18|18/1-36       TQTIYGQCGGTGYSGPTVCAGGSRCKQVNPHFSQCL
21|21/1-36       TQTLYGQCGGSGYSGPTRCAPPATCSTLNPYYAQCL
22|22/1-36       TQTLYGQCGGSGYSGPTRCAPPATCSTLNPYYAQCL
25|25/1-35       -QTVWGQCGGIGWSGPTNCAPGSACSTLNPYYAQCL
```

(Continued on next sheet)

US 8,506,717 B2

METHODS OF TREATING A BIOMASS FOR ENZYMATIC HYDROLYSIS

CROSS-REFERENCE TO RELATED APPLICATIONS

For purposes of United States patent practice, the contents of U.S. Provisional Application No. 61/266,618 filed Dec. 4, 2009 is herein incorporated by reference in its entirety to the extent that it is not inconsistent.

FIELD OF THE INVENTION

The present invention pertains to improved methods for treating a feedstock comprising holocellulose using, for example, a solution comprising cellulose binding domains prior to enzymatic hydrolysis.

BACKGROUND AND SUMMARY OF THE INVENTION

The enzymatic hydrolysis of cellulose to glucose has gained increased interest over the last ten years, and growing demand for economically sustainable biofuels points to an urgent need for reducing costs in their production. Cellulose, a polysaccharide made by many plants, is one of the most abundant organic compounds on Earth and therefore represents a potential goldmine for the biofuel industry. However, current enzymatic degradation of cellulose faces major issues that prevent its wide utilization to produce, for example, economically competitive biofuel. Such issues may include, for example, low reaction and/or conversion rates.

Advantageously, the inventors have discovered a process and composition which accomplishes the aforementioned goals and more. In general terms the instant invention pertains in one embodiment to a process for treating a feedstock comprising holocellulose. The process comprises mixing the feedstock with a solution comprising cellulose binding domains to form a mixture. The mixture is then subjected to conditions sufficient to reduce the crystallinity of holocellulose. Subsequent enzymatic hydrolysis may show an improved rate and/or fermentable sugar yield as compared to processes which do not employ the CBD treatment process.

DETAILED DESCRIPTION OF THE INVENTION

Figure 1:
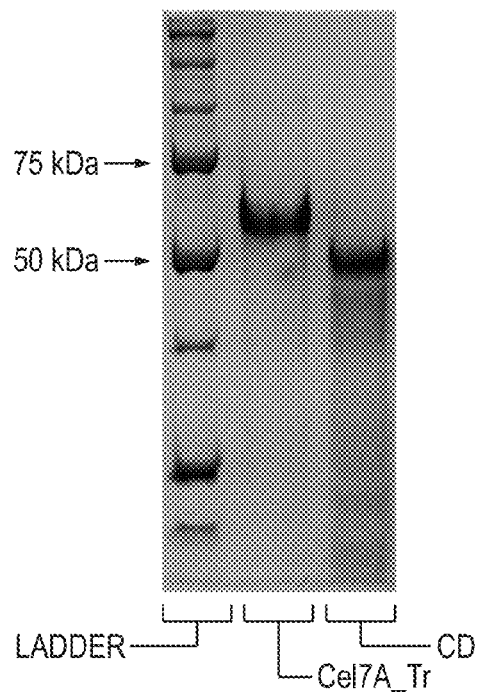
FIG. 1 illustrates an SDS-PAGE gel of purified cel7A from *Trichoderma reesei* and cel7A catalytic domain after papain cleavage.

In general terms the instant invention pertains in one embodiment to a process for treating a feedstock comprising holocellulose. The process comprises mixing the feedstock with a solution comprising cellulose binding domains to form a mixture. The mixture is then subjected to conditions sufficient to reduce the crystallinity of holocellulose. Subsequent enzymatic hydrolysis may show an improved rate and/or fermentable sugar yield as compared to processes which do not employ the CBD treatment process prior to a subsequent hydrolysis. Advantageously, the fermentable sugar in the hydrolyzed composition and/or the hydrolysis rate may be at least about 10%, or at least about 15%, or at least about 20%, more than a comparable process which does not employ cellulose binding domains. Following hydrolysis to produce one or more fermentable sugars such as glucose, processes such as fermentation may be employed to produce, for example, bioethanol.

Feedstock Comprising Holocellulose

The nature of the feedstock employed in the processes and compositions herein is not particularly critical so long as the feedstock comprises holocellulose. As used herein, "holocellulose" means at least a portion of the water-insoluble carbohydrate portion of a biomass, i.e., the portion of the biomass that is not lignin, extractives, or ash, but rather, includes substances such as polysaccharides. The precise, composition of holocellulose may vary depending upon the specific feedstock employed. However, holocellulose useful herein typically comprises various amounts of celluloses such as alpha-cellulose and hemicellulose and may contain various pentosan or hexosan polymers. Thus, virtually any lignocellulosic biomass that comprises cellulose may be employed as the feedstock in the processes and compositions of the instant invention. The invention may be advantageously employed on compositions comprising cellulose in which the crystallinity of the cellulose is in need of reduction.

In one embodiment a particularly preferable feedstock is a plant biomass. Biomass comes in many different types, which may be grouped into a few main categories: wood or forestry residues, including sawmill and paper mill discards, municipal paper waste, algae, agricultural residues, including corn stover (stalks and straw), and sugarcane bagasse, and dedicated energy crops, which are mostly composed of fast growing tall, woody grasses such as, for example, switchgrass.

Any of the aforementioned may find use in the instant invention. A particularly preferable biomass comprises one with high cellulose content.

Depending upon the nature of the feedstock it may be desirable to reduce at least a portion of it in size in order to expose additional surface area for treatment. Such reduction may be done in any convenient manner such as by grinding, cutting, chopping, etc. The desired size of the feedstock varies depending upon the type of ingredients and other specifics of the instant inventions. Typically, smaller size feedstocks may react quicker but cost more to produce. Generally, it is advantageous if the feedstock is reduced prior to CBD treatment and/or prior to hydrolysis.

Similarly, it is often advantageous, or may even be necessary, in some situations to first purify at least a portion of the feedstock. By purify is meant to partially clean in order to remove at least some contaminants that may negatively effect downstream processes. This purification may assist in reducing or eliminating any undesired reactions in the following steps. The type of purification will depend upon the source of the feedstock, as well as, the amount and nature of the impurities and the following steps to which it will be subjected. Often, simple washing of the lignocellulosic feedstock is sufficient. Such purification, if done, may be accomplished prior to, in conjunction with, or subsequent to any size reduction. Additionally, if desired or advantageous, at least a portion or all of the feedstock that does not comprise holocellulose may be separated. However, this is unnecessary for many processes and conditions to which the composition will likely be subjected.

Cellulose Binding Domain (CBD)

The cellulose binding domains employed herein are typically derived from cellulases. Cellulases are glycosyl hydrolases of varying structure which catalyze the hydrolysis of 1,4-β-D-glycosidic bonds. Most cellulases comprise three domains: (1) a catalytic domain which primarily serves as the locus of hydrolysis, (2) a cellulose-binding domain that often assists in anchoring the whole enzyme onto the cellulose surface and/or in orienting the cellulose fiber towards the tunnel containing the active site, and (3) a glycosylated flexible linker connecting the two other domains and often providing sufficient spatial separation between them. The linker may also assist in allowing processive motion and/or assisting in energy storage.

As used herein the term "cellulose binding domain" or "CBD" is a portion of cellulase that includes a substantial portion of the aforementioned (2) but lacks a substantial portion, the majority, or all of (1). Such cellulose binding domains in some embodiments include all or at least a portion of the linker (3) while in other embodiments the linker (3) is modified or absent from the cellulose binding domain employed. Thus, useful CBD for use herein may often be obtained from cellulase by cleaving CBD and, if desired, linker from the cellulase in a convenient method such as, for example, proteolytic cleavage. Depending upon the cleaving method, the CBD may then be recovered in a convenient manner such as, for example, filtration. In some embodiments, the ratio of cellulose binding domains to catalytic domain is greater than 1:1, or greater than 2:1, or greater than 3:1, or greater than 5:1, or greater than 10:1.

The nature and type of cellulose binding domain employed is not particularly critical so long as they function in some manner to reduce the crystallinity of cellulose and/or facilitate any further processing such as hydrolysis. Suitable CBSs may be derived from a suitable enzyme produced by a species like, for example, a *Trichoderma* species such as *T. reesei*, *T. viride*, as well as, for example, *Phanerochaete chrysasporium*, *Humicola insolens*, *Coprinopsis cinerea*, *Acremonium cellulolyticus*, *Hypocrea jecorina*, *Penicillium occitanis*, *Irpex lacteus*, *Penicillium* echinulatum, Lentinula edodes, Penicillium decumbens.

In one embodiment the cellulose binding domains are derived from cellobiohydrolase (cel7A) such as produced by, for example, a *Trichoderma* species like *Trichoderma reesei*. In another embodiment the cellulose binding domains are derived from cellobiohydrolase II (cel6A). In other embodiment the cellulose binding domains are derived, for example, from an enzyme in Table 5 below. In another embodiment the cellulose binding domains employed may be a mixture of two or more of the aforementioned. The CBD Cellulose-binding domains (CBDs) of cellulases from *Trichoderma reesei* (belonging to family I CBD) form a wedge-like fold, where a flat face provides key (aromatic) residues strongly interacting with crystalline cellulose. Such methods as those described in the below examples may be employed. In addition, with the benefit of the instant disclosure, one of skill may employ routine testing of other substances to identify useful materials. Alternatively or additionally, protein engineering may be conducted on CBD. Mutations of certain residues on CBD (such as those involved in binding or interacting with cellulose and/or any that may effect a faster hydrolysis rate) may then be exploited to develop CBD tailored to, for example, specific feedstocks and/or process conditions.

Mixing the Feedstock with a Solution Comprising Cellulose Binding Domains

The solution comprising cellulose binding domains may be made and mixed with the feedstock in any convenient manner. The concentration of the solution comprising cellulose binding domains varies depending upon the particular feedstock, other ingredients of the solution such as buffer, and the conditions to be employed. Generally, it should have a concentration at least sufficient to reduce the crystallinity of the cellulose at the treatment conditions but not so high that it interferes with any subsequent desired processing steps such as hydrolysis. Generally, a concentration of at least about 5, or at least about 10, or at least about 15 up to at most about 100, or at most about 75, or at most about 55, or at most about 45, or at most about 35 μg/ml may be effective. A suitable buffer may also be employed in the solution if desired. It may be advantageous to employ a buffer which acts synergistically with the CBD to even further facilitate reducing the crystallinity of the cellulose. Suitable buffers often include salts or esters of lower alkyl acids such as acetic acid and typically have a pH of from about 4.5 to about 5.5. In one embodiment, the solution comprises a sodium acetate buffer at a concentration of from about 25 to about 75 mM.

CBD Treatment Conditions

Once a mixture comprising one or more feedstocks with a solution comprising cellulose binding domains is made, then the mixture is subjected to conditions sufficient to reduce the crystallinity of holocellulose and/or facilitate a subsequent hydrolysis. These conditions may vary widely depending upon the nature and type of feedstock and the type and amount of ingredients in the solution comprising cellulose binding domains.

Typically, the mixture is subjected to an increased temperature for a time sufficient to reduce the crystallinity of holocellulose. Such temperatures vary but may be at least about 30° C., or at least about 35° C. up to at most about 60° C., or at most about 50° C., or at most about 45° C. Generally, the higher the temperature employed, the shorter the time that the mixture must be heated and vice versa. At the previously described temperatures, suitable times to which to subject the mixture to increased temperature at least about 8 hours, or at least about 10 hours, or at least about 12 hours, or at least about 14 hours, up to at most about 48 hours, or at most about 24 hours, or at most about 16 hours. Using the present disclosure, one of skill in the art may use routine experimentation to determine proper times and temperatures for a particular feedstock and composition.

Without wishing to be limited to any particular theory, it is believed that the cellulose binding domains and similar proteins reduces the degree of crystallinity, and therefore renders the cellulose less recalcitrant to enzymatic attack. The aforementioned processes of the instant invention may be used alone or in conjunction with other techniques to decrease the crystallinity to a desired level. Such techniques may be used before, during, or after the processes of the instant invention and include, for example, (thermo)chemical and/or mechanical techniques (e.g. treatment with phosphoric acid, ionic liquids or organic solvents, AFEX, and ball mill grinding). In some instances purification may be beneficial before the hydrolysis step (e.g. with ionic liquids). In some instances it may be advantageous to subject the mixture to sufficient stirring such that substantially all solids are suspended. For example, in some instances the mixture is subjected to stirring, preferably vigorous, in a vial with a stir bar. In some embodiments the stir bar has a diameter of at least about 45%, preferably at least about 50%, preferably at least about 55%, of the inner vial diameter.

In another embodiment, the instant invention pertains to the use of a solution or composition comprising cellulose binding domains in a pre-treatment step in, for example, a cellulose hydrolysis process. The solution or composition comprising cellulose binding domains is as described above and below. Similarly, the pre-treatment step is as described, i.e., first mixing a hollocellulosic feedstock with the solution or composition comprising cellulose binding domains to form a mixture and then subjecting the mixture to conditions sufficient to reduce the crystallinity of holocellulose. The specific ingredients, conditions, etc. may be as described elsewhere herein.

EXAMPLES 1-8

General Procedure for CBD Treatment of Avicel

Cellobiohydrolase I (cel7A) is a component of a cellulase mixture which is an exoglucanase which attacks cellulose chains from the reducing-end side. The following inventive examples employ the cellulose-binding domains (CBD) from this enzyme, and more specifically cel7A from *Trichoderma reesei*, a commonly used organism in the production of, for example, bioethanol. The effect of CBD on cellulose was investigated, i.e. the consequence of cellulose incubation, i.e., treatment, in a solution comprising CBD on the degree of crystallinity, and subsequently on the enzymatic hydrolysis rate of the reaction performed with the CBD-treated cellulose.

Cel7A is constituted of three domains: a cellulose-binding domain (CBD), a catalytic domain (CD) and a highly glycosylated linker that joins the CBD to the CD. The examples involve:

(1) producing CBD from cel7A, via proteolytic cleavage of that fragment (plus linker) from the CD using papain (a cysteine protease);
(2) recovering CBD via filtration through a 30 kDa membrane (CBD+linker~61 residues; theoretical size~6 kDa; estimated size from experiments~14 kDa due to O-glycosylation of the linker; estimated size of CD~50 kDa due to N-glycosylation);
(3) incubating, i.e., treating, cellulose (Avicel) with a solution comprising CBD; and
(4) adding cellulase cocktail (from *Trichoderma reesei*) and monitoring hydrolysis rate (via glucose content).

General Procedure for CBD Production

Following the procedure on CBD cleavage from the core protein as used in, for example, P. Tomme et al., *Eur. J. Biochem.*, 1988, 170, 575-581, papain was employed to perform the proteolytic digestion under the following conditions:

1. Activation of papain in 50 mM $NH_4OAc$ buffer pH 6.0 at 30° C. for 30 min;
2. Addition of papain to cel7A solution (in 50 mM NaOAc buffer, pH 5.0) at 30° C., ratio papain/cel7A 1:5 (w/w, v/v);
3. Stirring for 2 h at 30° C.; and
4. Filtration of the reaction mixture through 30 kDa membrane (4000 rpm for 15 min) to collect the cellulose binding domain (attached to the linker) in the filtrate.

The cleavage reaction was found to be complete after 2 h, and no remaining cel7A (~64 kDa) could be detected by SDS-PAGE as shown in FIG. 1. The reaction led to the formation of a single strong band, with a molecular weight of 50 kDa. The papain successfully cleaved off CBD+linker from the core protein (CD); however, this small protein fragment (~14 kDa) was not detected by SDS-PAGE (the sequence shows very few residues that can react with commonly used Coomassie dye-staining). However, CBD was detected via micro BCA protein assay (bicinchoninic acid) in the filtrate (<30 kDa) (Table 1, 100% recovery).

TABLE 1

Cel7A fragments recovery after papain cleavage

| Protein fragments | Total mass (mg) |
|---|---|
| Cel7A (+papain) before reaction | 4.6 mg |
| CD (+papain) concentrate after filtration through membrane >30 kDa | 3.8 mg |
| CBD filtrate after filtration through membrane <30 kDa | 0.6 mg |
| Expected CBD (~10-14 kDa from 64 kDa) | 0.6-0.9 mg |

Example 1A

Avicel Treatment with a Solution Comprising Cellulose Binding Domain (CBD) and Measurement of Crystallinity Via X-Ray Diffraction While not wishing to be bound to any particular theory it is believed that the activity of CBD relates to non-hydrolytic disruption of cellulose and a weakening and splitting of the hydrogen-bonding network in cellulose. The following investigation determined whether that activity was strong enough to reduce cellulose crystallinity.

Avicel was treated with CBD solution (obtained as described above), and the degree of crystallinity of the recovered cellulose was subsequently determined via X-ray diffraction using our recently developed analytical method described in, for example, Bansal et al., Multivariate statistical analysis of X-ray data from cellulose: A new method to determine degree of crystallinity and predict hydrolysis rates. *Bioresource Technol.*, 101, 4461-4471.

The cellulose treatment step was performed as follows: Avicel (20 mg/ml) in CBD solution (50 mM NaOAc buffer, pH 5) was stirred at 37° C. for 2 days. The mixture was centrifuged at 4000 rpm for 15 min and recovered cellulose was freeze-dried. The powder was analyzed by the X-ray diffraction method referred to above.

Avicel is a microcrystalline cellulose with an average degree of crystallinity of about 60%. Upon treatment with the CBD solution, a significant decrease in Avicel crystallinity was observed as shown in Table 2 below. The highest decrease of 13% was obtained with sample 4 which corresponded to 4.7 ml of filtrate obtained from the cleavage of 3.3 mg cel7A in 7 ml buffer.

TABLE 2

Degree of crystallinity (CrI) of Avicel after incubation (2 days) with cellulose-binding domain (CBD) or catalytic domain (CD)

| CrI (%)* | CBD | CD | No treatment prior to hydrolysis |
|---|---|---|---|
| 1 | 57.2 | 59.6 | 60% |
| 2 | 57.4 | 60.3 | |
| 3 | 56 | 61 | |
| 4 | 52 | 62 | |

Figure 2:
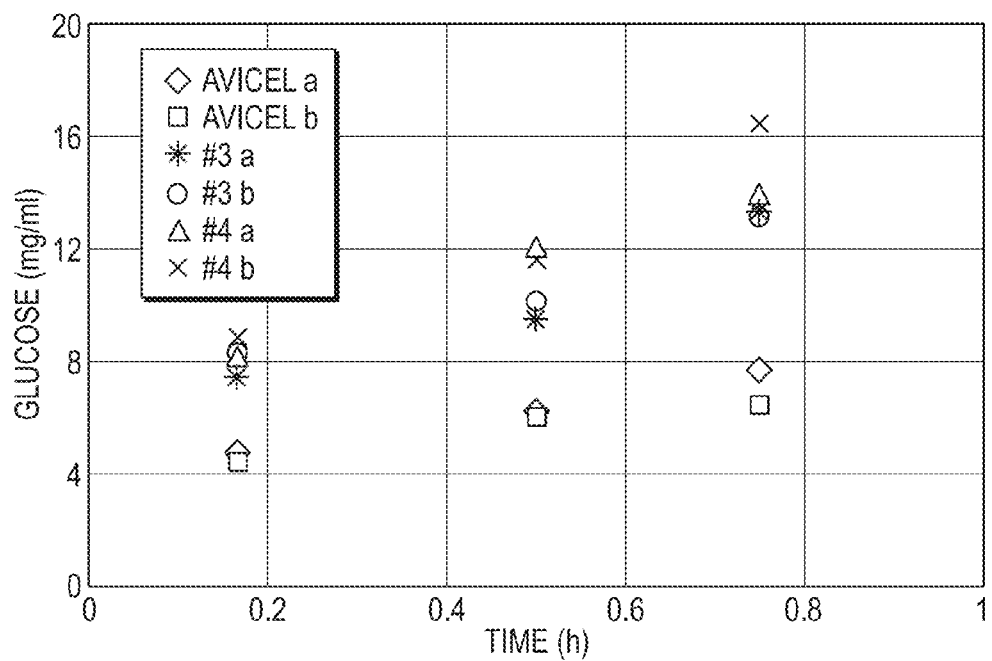
FIG. 2 illustrates the enzymatic hydrolysis of Avicel after CBD treatment.

*samples 1-4 refer to different experiments. 1 and 2 were run at low CBD concentrations, 3-4 at higher CBD concentration Example 1B Enzymatic Hydrolysis of CBD Treated Samples of Example 1A The cellulose samples (3 and 4, Table 2) that presented a significant lower crystallinity value compared to untreated Avicel were submitted to enzymatic hydrolysis using the cellulase cocktail from *Trichoderma reesei* (supplemented with β-glucosidase to prevent product inhibition). A significant increase in rate was observed for the samples treated with CBD solution prior to hydrolysis, with an overall rate 2-fold higher than that of untreated Avicel over the course of the reaction as shown in FIG. 2. Thus, the decrease in crystallinity observed after treating Avicel with CBD solution correlated well with a decreased recalcitrance to enzymatic attack, and therefore a faster conversion to glucose.

General Procedure to Measure Effect of Various CBD Treatment Conditions

The following shows the effect of various CBD treatment conditions on hydrolysis rates. As crystallinity was shown to decrease, no additional crystallinity measurement was conducted and therefore cellulases were directly added to the reaction mixture after CBD treatment time was over, i.e. the samples were not freeze-dried before investigation of hydrolysis rates, nor was the buffer exchanged or the solution diluted. The sequential CBD treatment and hydrolysis process was performed as followed:
1. Incubating Avicel with CBD solution over various time lengths at 37° C.;
2. Changing temperature to 50° C.;
3. Adding cellulase cocktails and β-glucosidase and stirring at 50° C.; and
4. Withdrawing reaction mixture aliquots for glucose quantification at various time intervals.

Example 2

Effect of Incubation Time, CBD Concentration, and Buffer on Hydrolysis Rate

Figure 3:
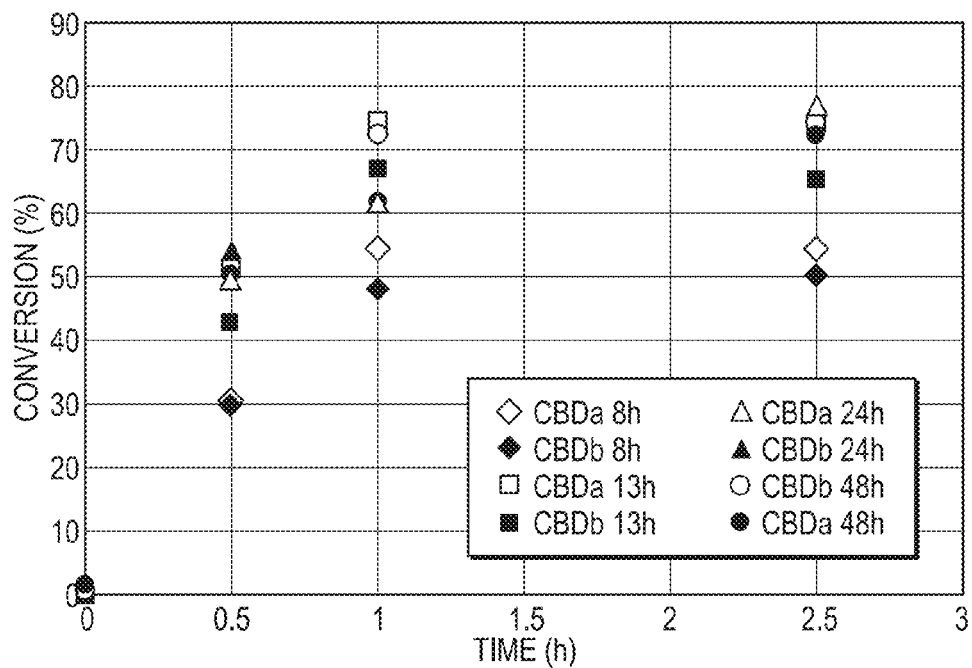
FIG. 3 illustrates the effect of various CBD incubation times.

To find more optimum CBD treatment times that would lead to a higher increase in hydrolysis rate, the 48 h incubation time that led to the 13% decrease in crystallinity (see above) was varied from 8 h to 24 h and the enzymatic hydrolysis rates were examined. One single CBD solution was used throughout these experiments, so that they were performed at constant CBD concentration (~42 μg/ml). Positive effects of CBD were obtained between 8 h and 13 h of incubation at 37° C. Beyond 13 h, no further increase in rates was observed as shown in FIG. 3. Depending on the incubation time, a maximum of 20-25 percentage points difference was observed in glucose content (corresponding to 50-60% increase in rate between the 8 h and >13 h CBD treatment times).

Figure 4:
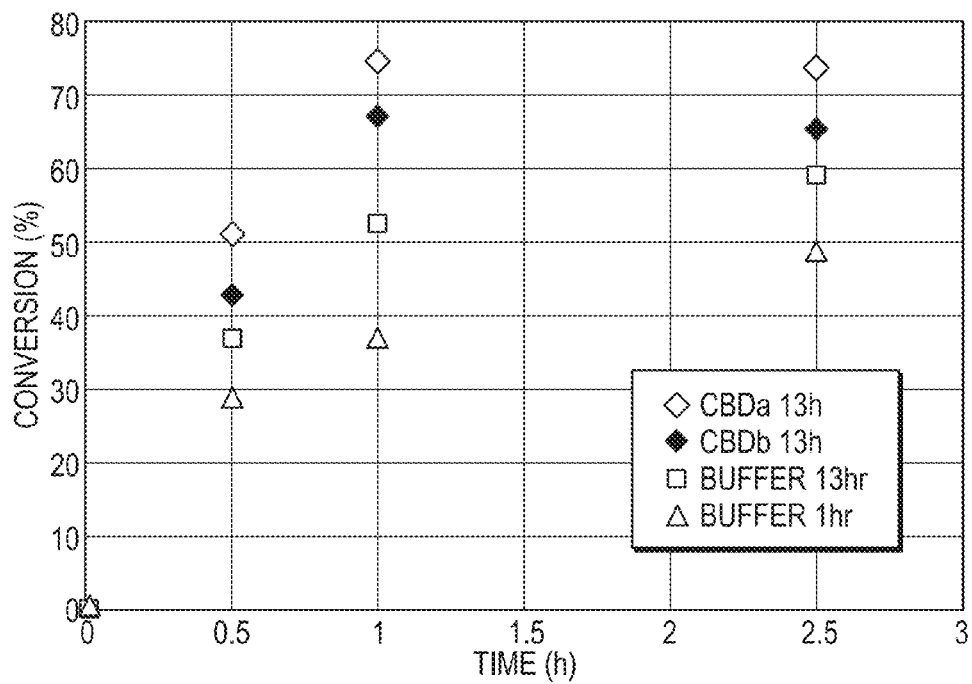
FIG. 4 shows the effect of buffer incubation on hydrolysis rate compared to CBD incubation (13 h).

However, incubation in buffer was found to also have a positive effect on hydrolysis rate. Despite lower conversion compared to incubation with CBD solution, conversion on sample incubated in buffer for 13 h was higher than after 1 h incubation in buffer as shown in FIG. 4. When conversion on CBD treated sample was up to two-fold higher than that on buffer-treated sample for 1 h (after 1 h hydrolysis), the difference was less significant between the CBD treated sample and the buffer treated sample for 13 h (1.3-1.4 fold higher).

Figure 5:
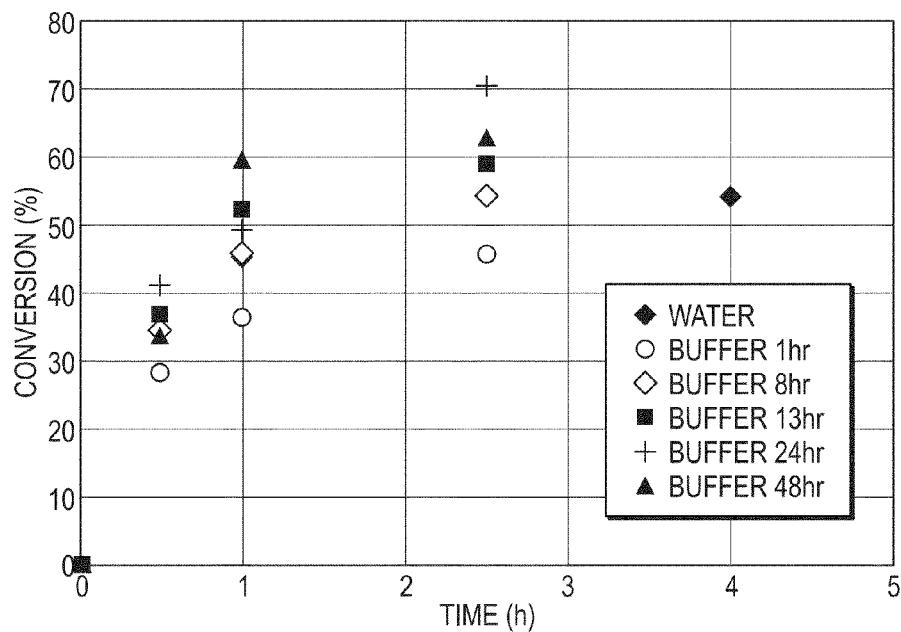
FIG. 5 shows the effect of buffer incubation time on hydrolysis rates.

The effect of buffer on hydrolysis rate was shown to be time-dependent, however, no major difference was observed between 13 h and 48 h of incubation in buffer, although an incubation for 24 h led to the highest rates as shown in FIG. 5. Interestingly, water incubation (18 h) showed a positive effect on rate (higher conversion than with 1 h incubation in buffer), however, less pronounced than with similar incubation time in buffer. A pH shift is suspected, as water had a pH of 5.5, 0.5 units higher than the pH of the buffer (50 mM NaOAc pH 5).

Crystallinity measurements were then conducted on cellulose samples preincubated in buffer only and water only, respectively. No significant change from the untreated Avicel was observed after 24 h incubation at 37° C. (apart from a slight increase in crystallinity up to 63%, which should not relate to an increase in rate in many cases).

Figure 6A:
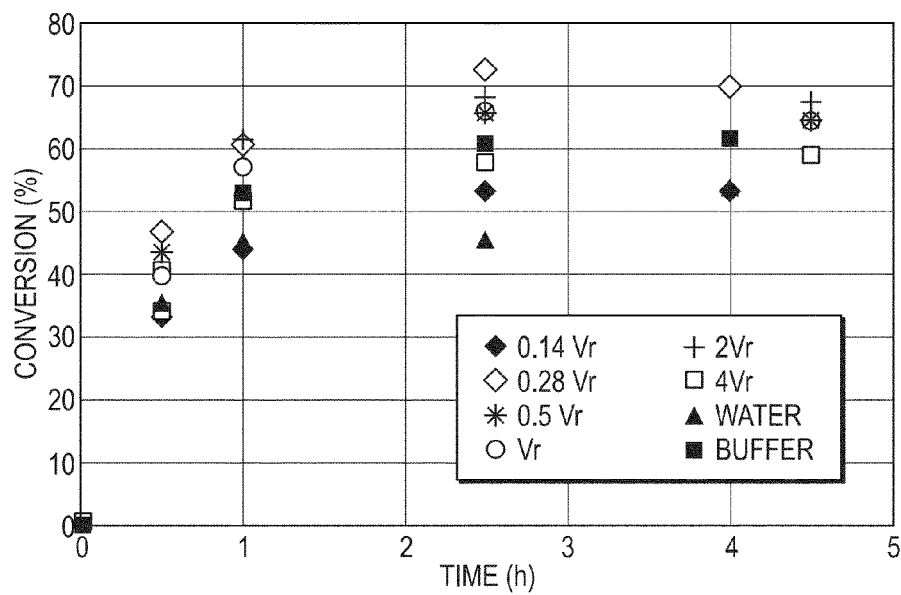
FIG. 6 shows the results of a CBD concentration optimization experiment.
Figure 6B:
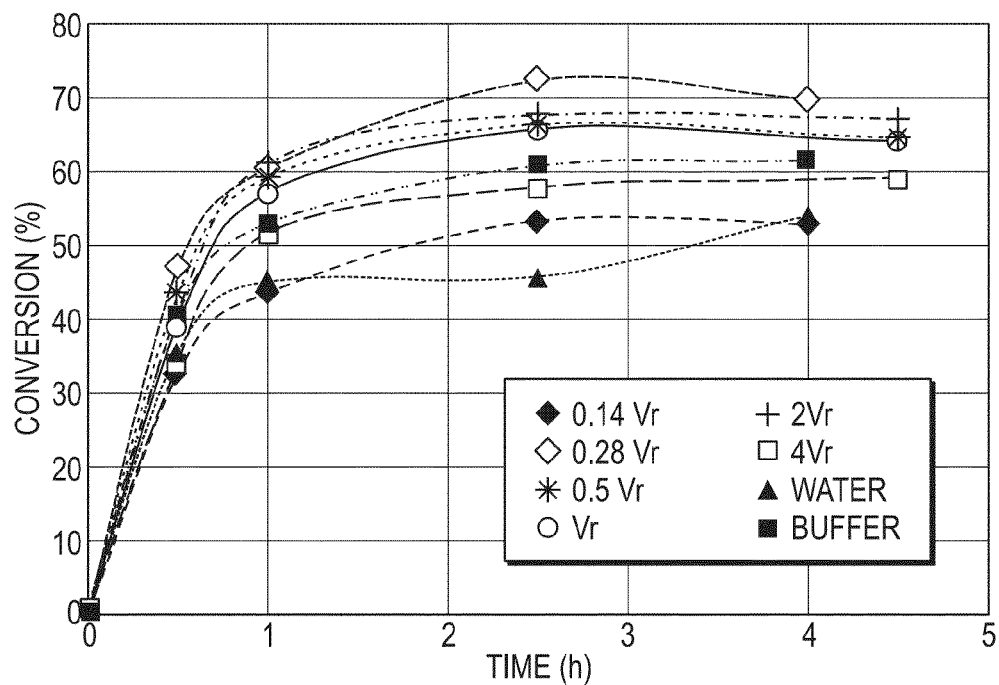

Next, the CBD concentration was varied, starting from a reference volume (Vr added to the reaction mixture, corresponding to a final CBD concentration of 24 μg/ml). Higher concentrations (up to 4 Vr) and lower concentrations (down to 0.14 Vr) were examined. Overall, the effect of CBD was less pronounced than in the previous examples as shown in FIG. 6.

The highest rates were obtained with 0.28 Vr, whereas both lower and higher concentrations (0.14 Vr and 4 Vr resp.) led to lower conversion. At higher CBD conversion, where cellulases added to perform hydrolysis have less binding spots available on cellulose surface due to the presence of multiply-bound CBDs, competitive adsorption between CBD and cellulases occurs. No major difference was found between 0.5 and 2 Vr. The lowest CBD concentration (0.14 vr) performed similarly to water, and the highest CBD concentration (4 Vr) performed similarly to the buffer.

CBD Production for the CBD of Examples 3-8

The CBD employed in Examples 3-6 was made as follows: Cel7A was obtained from a mixture of cellulases from *Trichoderma reesei* and purified by means of anion exchange column chromatography using a HiPrep Q FF column. The purified protein was cleaved by proteolysis using papain and the cellulose binding domain (attached to the linker) was separated from the catalytic domain by centrifugation through a 30 kDa membrane and collected in the filtrate at a concentration of 125-175 μg/ml.

Example 3

Effect of CBD Treatment Time

Avicel (20 mg/ml) was incubated in buffer (NaOAc 50 mM pH 5.0) together with CBD (24 μg/ml) at 37° C. and under gentle stirring in a 24 ml glass vial. The effect of treatment was investigated over various time periods (8 h, 13 h, 24 h and 48 h).

Hydrolysis of cellulose was performed on the CBD treated Avicel (20 mg/ml) by addition of cellulases (24 µl/ml, 3.4 mg/ml total protein, 3.8 FPU/ml) and β-glucosidase (15 U/ml) to the mixture and the reaction was carried out at 50° C. Glucose production was monitored by the DNS assay at various intervals (1 h, 2.5 h and 4 h). Controls were run on dry Avicel (no CBD treatment) and on samples incubated in buffer only (for 1 h, 13 h and 48 h).

Figure 7:
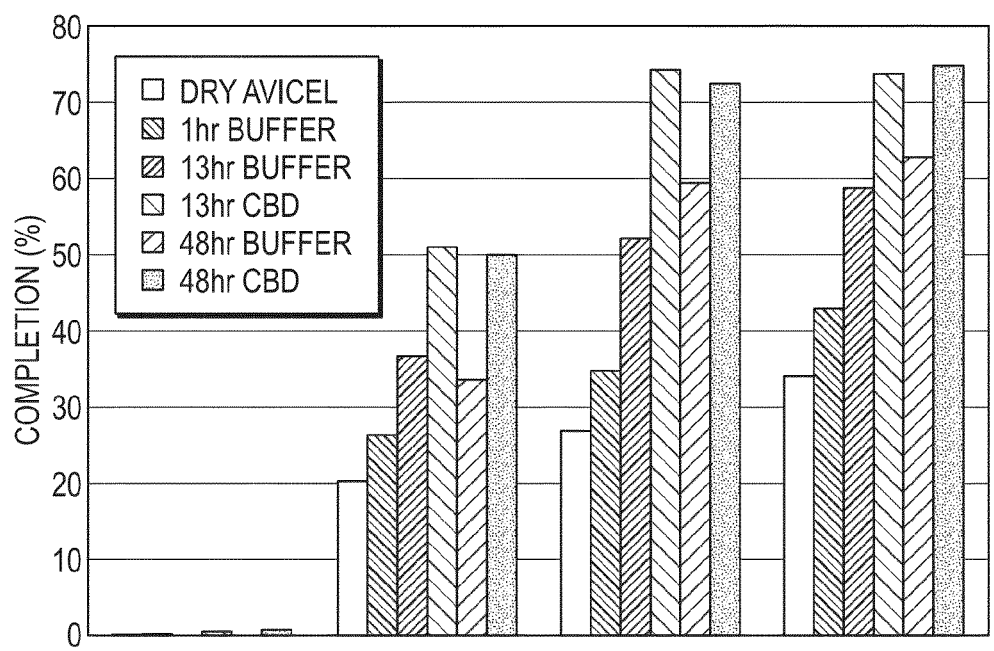
FIG. 7 shows hydrolysis for various CBD treatment times.

The incubation in buffer was found to be beneficial to the hydrolysis, as a higher glucose concentration was obtained already after 1 h incubation compared to hydrolysis on dry cellulose. The effects were more pronounced after a 13 h incubation, and no further increase was obtained up to 48 h. Incubation of Avicel in CBD gave a surprising and unexpected increase compared to the buffer alone (20-35%). The CBD treatment reached a maximum effect after 13 h incubation. The results are shown in FIG. 7.

Example 4

Effect of CBD Concentration

Figure 8:
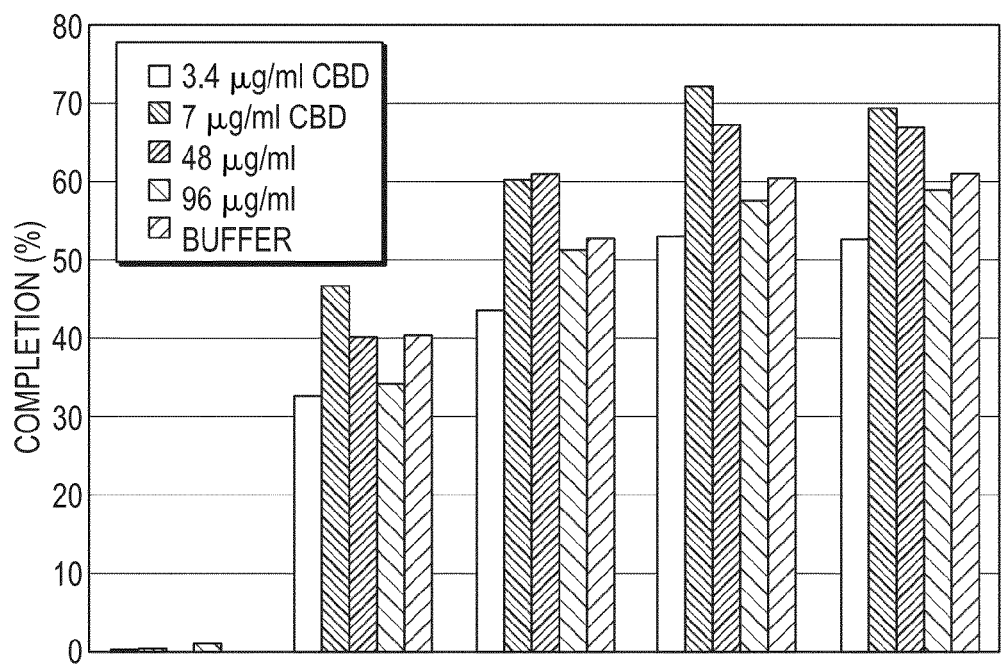
FIG. 8 shows the effect of various concentrations of CDB.

Avicel (20 mg/ml) was incubated in buffer (NaOAc 50 mM pH 5.0) together with CBD at various concentrations (3.4, 6.9, 12, 24, 48 and 96 µg/ml) at 37° C. and under gentle stirring for 18 h in a 24 ml glass vial. Hydrolysis of cellulose was performed on CBD treated Avicel (20 mg/ml) by addition of cellulases (24 µl/ml, 3.4 mg/ml total protein, 3.8 FPU/ml) and β-glucosidase (15 U/ml) to the mixture and the reaction was carried out at 50° C. Glucose production was monitored by the DNS assay at various intervals (1 h, 2.5 h and 4 h). The effect of CBD incubation on cellulose hydrolysis was found to be better at 7 µg/ml, up to 48 µg/ml, whereas higher concentrations gave a lower increase in glucose production, especially at 96 µg/ml where the treatment was less efficient than in buffer only. The results are shown in FIG. 8.

Example 5

Effect of Sequential Addition

Avicel (30 mg/ml) was incubated in buffer (NaOAc 50 mM pH 5.0) at 37° C. and under gentle stirring for 18 h in a 24 ml glass vial, followed by the addition of a CBD solution in same buffer (48 µg/ml), corresponding to a final concentration of Avicel of 20 mg/ml. The mixture was stirred for another 12 h at 37° C.

Hydrolysis of cellulose was performed on CBD treated Avicel (20 mg/ml) by addition of cellulases (24 µl/ml, 3.4 mg/ml total protein, 3.8 FPU/ml) and β-glucosidase (15 U/ml) to the mixture and the reaction was carried out at 50° C. Glucose production was monitored by the DNS assay at various intervals (1 h and 2.5 h).

The sequential addition of CBD after first incubating in buffer only led to higher conversion than simultaneous incubation in buffer and addition of CBD. This effect was more pronounced at higher degrees of conversion (about 35% higher glucose production compared to incubation in buffer only after 2.5 h hydrolysis). The results are shown in combination with the results of Example 6 at FIG. 9.

Example 6

Effect of CBD Removal

Avicel (20 mg/ml) was incubated in buffer (NaOAc 50 mM pH 5.0) together with CBD at various concentrations (6.9 and 48 µg/ml) at 37° C. and under gentle stirring for 18 h in a 24 ml glass vial. The CBD adsorbed onto cellulose was removed by heating up the cellulose (recovered by centrifugation) in 1.1% SDS solution, followed by multiple washings with EtOH (75%) and water.

Hydrolysis of cellulose was performed on CBD treated and washed Avicel by addition of cellulases (24 µl/ml, 3.4 mg/ml total protein, 3.8 FPU/ml) and β-glucosidase (15 U/ml) to a solution of cellulose (20 mg/ml) in buffer (NaOAc 50 mM pH 5.0) and the reaction was carried out at 50° C. Glucose production was monitored by the DNS assay at various intervals (1 h and 2.5 h).

The CBD removal procedure had a detrimental effect on cellulose hydrolysis, as the amount of glucose produced was significantly lower than that obtained after treatment with CBD with no removal, and slightly lower than that obtained after incubation in buffer only. The results are shown in combination with the results of Example 5 at FIG. 9.

Example 7

Effect of Incubation Temperature

Avicel (20 mg/ml) was incubated in buffer (NaOAc 50 mM pH 5.0) together with CBD at various concentrations (24 and 48 µg/ml) and temperatures (45 and 50° C.) and under gentle stirring for 24 h in a 24 ml glass vial.

Hydrolysis of cellulose was performed on CBD treated Avicel (20 mg/ml) by addition of cellulases (24 µl/ml, 3.4 mg/ml total protein, 3.8 FPU/ml) and β-glucosidase (15 U/ml) to the mixture and the reaction was carried out at 50° C. Glucose production was monitored by the DNS assay at various intervals (1 h, 2.5 h and 4 h).

Figure 10:
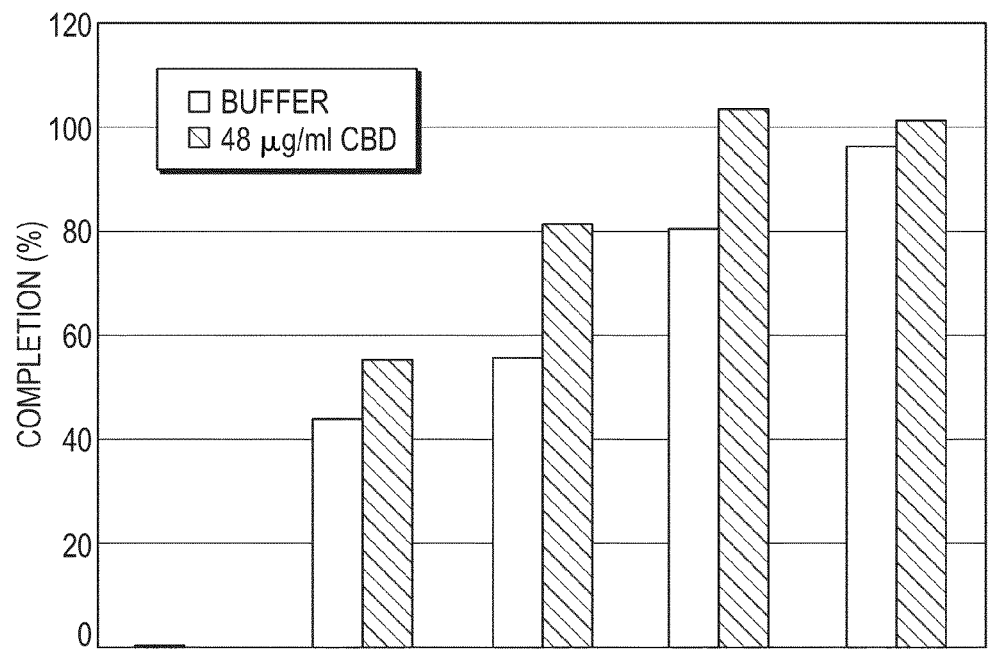
FIG. 10 shows the effect of a 45° C. treatment.
Figure 11:
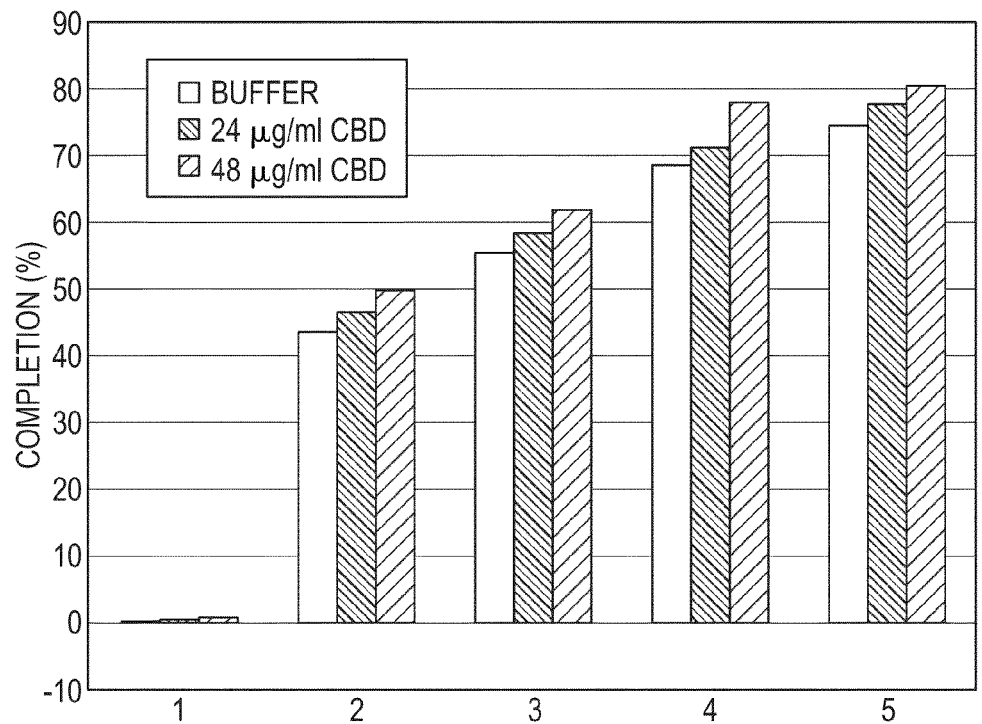
FIG. 11 shows the effect of a 50° C. treatment.

Treatment with CBD at 45° C. led to higher glucose production compared to 37° C., whereas 50° C. showed lower glucose production compared to 45° C. At 50° C., the CBD concentration effect differed from the one at 37° C.: CBD incubation at 24 µg/ml was less efficient than at 48 µg/ml. In addition, CBD incubation at 48 µg/ml performed less good than at 45° C. The results are shown in FIGS. 10 and 11.

Example 8

Treatment of Switchgrass with CBD

The treatment based on cellulose-binding domain (CBD) from cellobiohydrolase I (Cel7A) from *Trichoderma reesei* was applied to lignocellulosic materials (switchgrass), followed by the addition of cellulases to the CBD treatment mixture to perform hydrolysis. This led to an increase in lignocellulose enzymatic hydrolysis compared to no treatment with CBD ("dry sample") prior to hydrolysis, as measured as the amount of reducing ends produced over time.

Briefly, switchgrass (20 mg/ml) was incubated at 45° C. in sodium acetate buffer (pH 5.0, 50 mM) supplemented with CBD (24 µg/ml) and under gentle stirring in a 24 ml glass vial for 16 h. The hydrolysis was performed on CBD-treated switchgrass (20 mg/ml) by addition of cellulases (24 µl/ml, 3.4 mg/ml total protein, 3.8 FPU/ml) and β-glucosidase (15 U/ml) to the mixture and the reaction was carried out at 50° C. The effect of CBD treatment was investigated by measuring the amount of reducing ends produced over time (as equivalents of glucose) using the DNS assay at various intervals (1 h, 2.5 h, 4 h and 6 h). Controls were run on dry switchgrass (no CBD treatment), dry switchgrass with simultaneous addition of CBD and cellulases and on samples incubated in buffer only (for 16 h).

Figure 12:
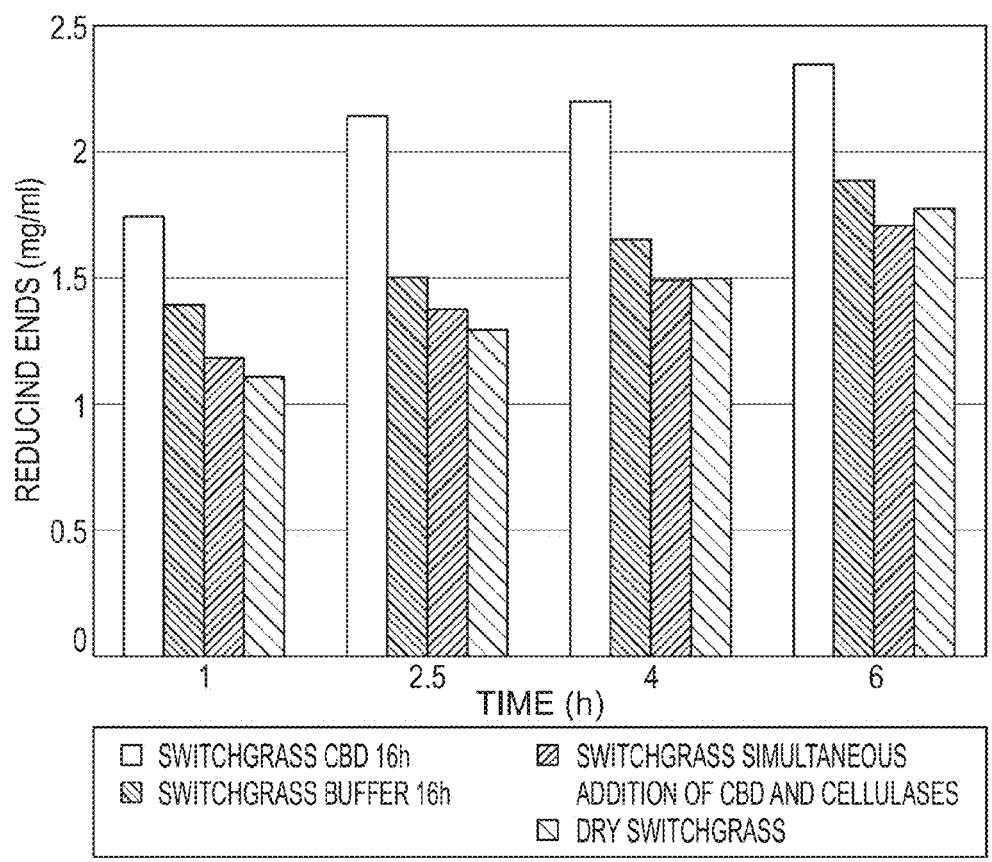
FIG. 12 shows the amount of reducing ends produced from switchgrass using cellulases and β-glucosidase after treatment with CBD, treatment with buffer, no treatment with simultaneous addition of CBD, and no treatment (dry sample).

The incubation in buffer was found to be slightly beneficial for hydrolysis, as a higher reducing end concentration was obtained after 16 h incubation compared to hydrolysis on dry switchgrass (maximum 25% increase after 1 h conversion). The effects were much more pronounced when CBD was present in the incubation mixture (up to 65% increase in reducing end concentration after 2.5 h conversion compared to dry sample). After 16 h incubation of switchgrass with CBD, the reducing end concentration presented a substantial increase compared to the one obtained after incubation in buffer alone (40-45% after 2.5 h conversion). Simultaneous addition of CBD and cellulases did not yield any difference in conversion compared to the dry sample. The results are shown in FIG. 12.

Example 9

CBD Treatment of Avicel and Fibrous Cellulose from Cotton Linters

Avicel PH-101, fibrous cellulose from cotton linters (Sigma C6288, medium), cellulases from *Trichoderma reesei* (159 FPU.mL$^{-1}$)), and β-glucosidase (from almonds, 2.32 U.mg$^{-1}$)) were obtained from Sigma (St Louis, Mo., USA). The (micro) BCA protein assay kit and the Coomassie (Bradford) protein assay kit were obtained from Thermo Fischer Scientific (Rockford, Ill., USA). Papain was obtained from Fluka as lyophilized powder from *Carica papaya* (9.84 U.mg$^{-1}$). Centrifugal devices with polyethersulfone membranes were from Pall Life Sciences (Ann Arbor, Mich., USA). All experiments and assays were run at least in duplicate.

Cel7A Purification

Cel7A was purified from *Trichoderma reesei* cellulase cocktail by means of anion-exchange chromatography as published in, for example, Hall et al., 2010. Cellulose crystallinity—a key predictor of the enzymatic hydrolysis rate. *Febs Journal*, 277, 1571-1582. Purity was confirmed by SDS-PAGE. After purification, Cel7A buffer was exchanged to sodium acetate buffer (50 mM, pH 5) using a polyethersulfone membrane (molecular weight cut-off of 10 kDa) in a Macrosep device.

Cellulase Proteolysis and CBD Isolation

Cellulase cleavage using papain was adapted from procedures published at, for example, Lemos et al., 2000. A simple method to separate cellulose-binding domains of fungal cellulases after digestion by a protease. *Biotechnology Letters*, 22, 703-707. Cellulase preparation (mixture from *Trichoderma reesei*) was diluted (5×) in sodium acetate buffer (50 mM, pH 5) and concentrated in a Jumbosep centrifugal device (polyethersulfone membrane, molecular weight cut-off of 30 kDa) to remove smaller molecules. Papain was activated in ammonium acetate buffer (50 mM, pH 6) at 30° C. and 170 rpm for 30 min and added to the cellulase solution (w/w 1:5, v/v 1:5). The digestion was performed at 30° C. for 2 h (completion checked via SDS-PAGE). The mixture was then filtered through 30 kDa membrane and both filtrate and concentrate were analyzed for protein content using the micro BCA assay.

X-Ray Diffraction and Crystallinity Measurement

X-ray diffraction patterns of cellulose samples (buffer and CBD pretreated) obtained after freeze-drying (at −55° C. and 0.03 mbar for 16 hours) were recorded with an X'Pert PRO X-ray diffractometer (PANanalytical BV, Almelo, the Netherlands) at room temperature from 10 to 35° C., using Cu/Kα$_1$ irradiation (1.54 Å) at 45 kV and 40 mA. The scan speed was 0.021425°.s$^{-1}$ with a step size of 0.0167°. The crystallinity index of cellulose was measured from X-ray diffraction data using an analytical method described at, for example, Bansal et al., Multivariate statistical analysis of X-ray data from cellulose: A new method to determine degree of crystallinity and predict hydrolysis rates. *Bioresource Technol.*, 101, 4461-4471.

Cellulose Pretreatment and Hydrolysis

Cellulose-binding domains were added in various amounts (up to 12 µg.mg$^{-1}$) to cellulose (Avicel or fibrous cellulose, total 56 mg, 40 mg.mL$^{-1}$) in sodium acetate buffer (50 mM, pH 5) in a glass vial (containing a stir bar). The mixture was incubated for 15 h at various temperatures in a shaker incubator at 170 rpm and was then diluted with buffer to lower cellulose concentration to 20 mg.mL$^{-1}$ for subsequent hydrolysis. Hydrolysis was initiated after the pretreatment step by adding cellulases (24 mL.L$^{-1}$, 3.4 g.L$^{-1}$ total protein) and β-glucosidase (15 kU.L$^{-1}$) to the reaction mixture, and was carried out at 50° C. and 170 rpm. The course of the reaction was monitored by performing DNS assay on small aliquots taken after 30 min, 1 h, and 2.5 h as described in, for example, Hall et al., 2010. Cellulose crystallinity—a key predictor of the enzymatic hydrolysis rate. *Febs Journal*, 277, 1571-1582.

For the thermostability experiment, cellulases and catalytic domains were incubated at 50° C. for 15 h and then added (300 µg.mL$^{-1}$ and 125 µg.mL$^{-1}$, resp.) to a cellulose mixture (Avicel, 20 mg.mL$^{-1}$ in sodium acetate buffer, 50 mM, pH 5) that had been incubated at 50° C. for 1 h at 900 rpm. The hydrolysis was run at 50° C. and 900 rpm and the conversion was monitored after 6 h and 22 h by performing DNS assay on the supernatant.

Enzyme Adsorption Experiments

Avicel samples (20 mg.mL$^{-1}$) in sodium acetate buffer (50 mM, pH 5) were incubated at 50° C. for 1 h at 900 rpm, and then cooled down to 4° C. Cellulases (which had been incubated in sodium acetate buffer at 50° C. for 15 h or stored at 4° C. since purchase) were added in various amounts and the mixture was further agitated for 30 min at 4° C. After centrifugation, the supernatant was collected and protein content analysis was performed using the BCA protein assay kit.

Results of Example 9

Cellulase Proteolysis and CBD Isolation

Figure 13:
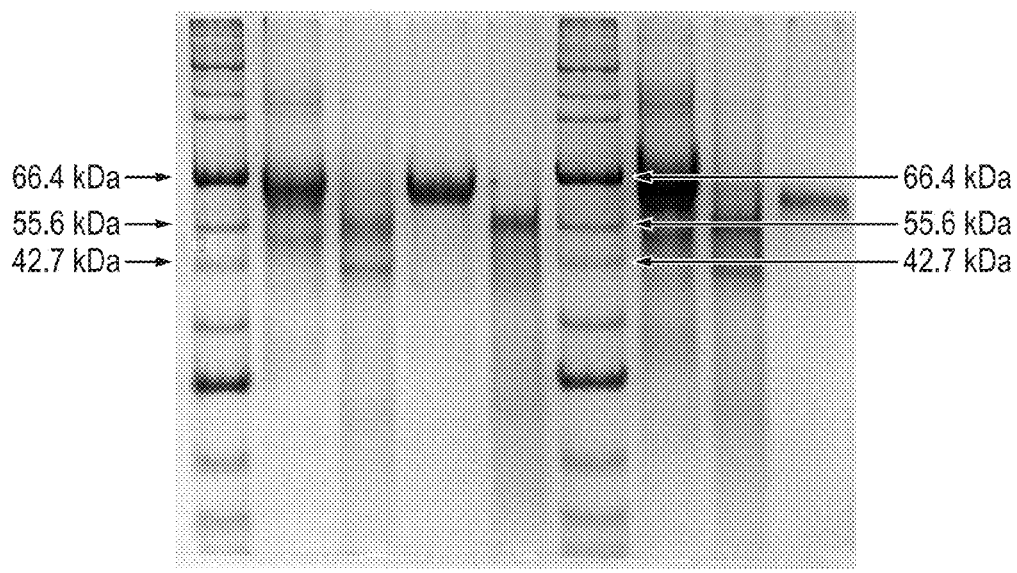
FIG. 13 shows the SDS-PAGE before and after papain cleavage of cellulases.

Both cellulase mixture (endoglucanases and exoglucanases) and purified cellobiohydrolase Cel7A from *Trichoderma reesei* were used in the proteolysis experiment using papain as cleaving agent. Cleavage was complete in both cases (as observed by the disappearance of full-length enzymes) and isolation of CBD through filtration yielded a mixture of CBDs or pure CBD$_{Cel7A}$, and corresponding catalytic domains (CDs) from the retentate could be observed by SDS-PAGE as shown in FIG. 13.

Cellulose Incubation with CBDs and Crystallinity

In Example 9, vigorous stirring was provided using a shaker incubator and the addition of a stir bar to the system. The high crystalline content of Avicel (CrI 60%) and fibrous cellulose (CrI 72%) allows for monitoring of changes occurring during pretreatment. After pretreatment of cellulose with CBDs in buffer at 42° C. for 15 h under vigorous agitation, the samples were collected and their crystallinity content was assessed by X-ray diffraction (XRD), while the supernatant was analyzed for the presence of soluble reducing ends. No reducing ends were released from the buffer control sample. While the amount of soluble reducing ends obtained with CBDs was very low (<120 µg.mL$^{-1}$, starting from cellulose concentration at 20 mg.mL$^{-1}$), it was consistent and above buffer background. Family I CBDs most likely do not have any hydrolytic activity; rather, small soluble oligomers were released from the cellulose surface upon binding/processing of CBDs. No disrupting activity could be observed e.g., no agglomerate formation nor faster precipitation without CBDs). After incubation in buffer only (control), the crystallinity of both types of cellulose (Avicel and fibrous) was shown to have slightly increased as shown in Table 3 below.

TABLE 3

Effect of 15 h incubation with buffer and cellulose-binding domains on cellulose crystallinity (CrI) as determined via X-Ray diffraction.

| Cellulose substrate | Avicel | Fibrous cellulose |
|---|---|---|
| CrI on dry sample (untreated) | 60% | 72% |
| CrI after incubation in buffer[a] | 65% | 74% |
| CrI after pretreatment with CBDs | 58% | 68% |
| CrI after pretreatment with $CBD_{Cel7A}$[b] | 53-56% | n.d. |
| CrI after incubation with $CD_{Cel7A}$[b] | 64% | n.d. |

Figure 14:
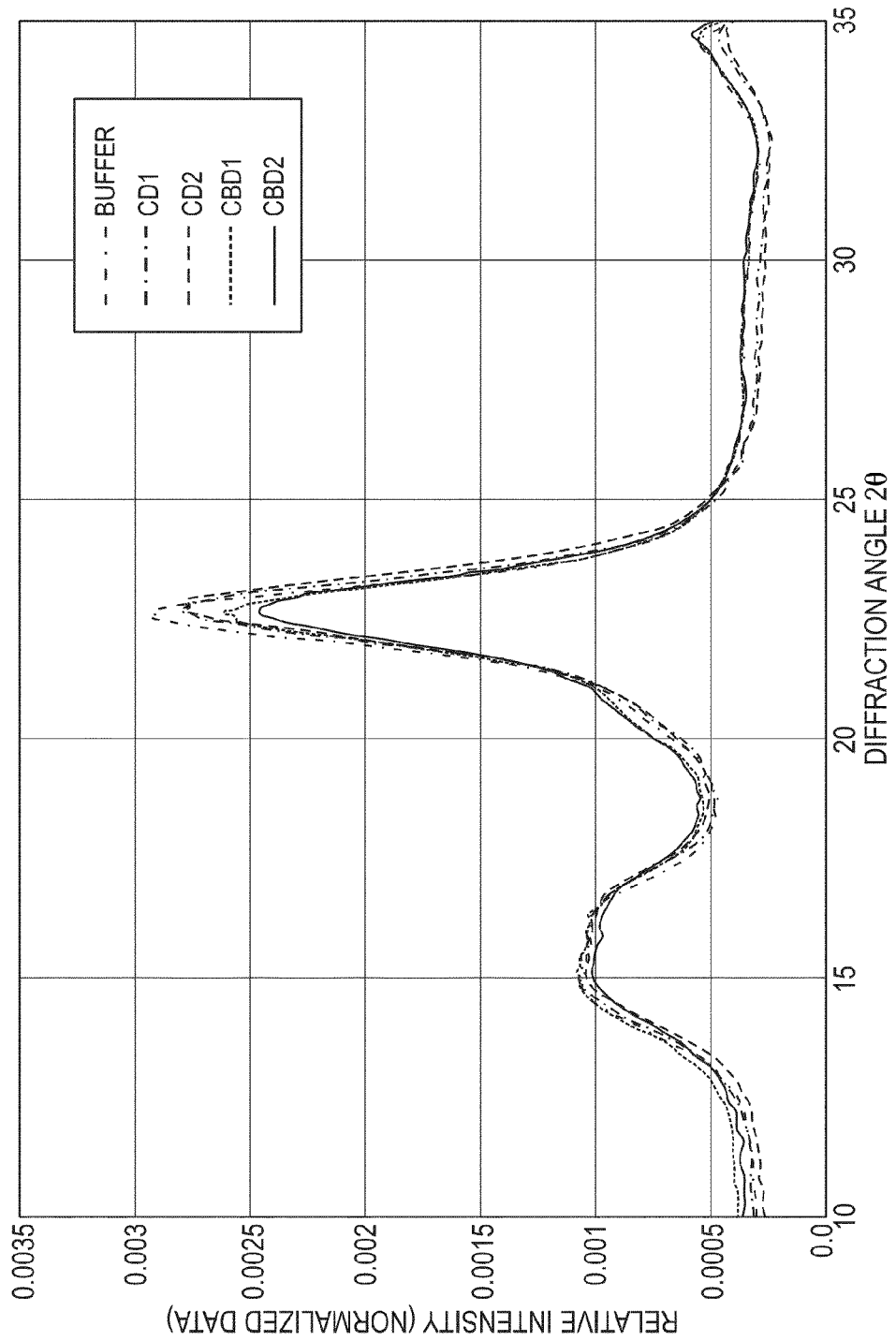
FIG. 14 shows the XRD spectra for Avicel samples treated with $CBD_{Cel7A}$ (cellulose-binding domain from purified Cel7A), $CD_{Cel7A}$ (catalytic domain) or buffer.

[a]Sodium acetate (pH 5.0, 50 mM).
[b]Longer incubation times (>48 h).
n.d. Not determined While not wishing to be bound to any particular theory, the crystallinity increase could be due to a phenomenon referred to as "recrystallization" described in, for example, Ouajai, S., Shanks, R. A., 2006. Solvent and enzyme induced recrystallization of mechanically degraded hemp cellulose. *Cellulose*, 13, 31-44. The increase (from 60% up to 65-66% on average for Avicel, and 72% up to 74% for fibrous cellulose) is not likely attributable to the removal of non-crystalline material from cellulose, as no soluble reducing ends were released in the buffer control sample. Also, the freeze-drying does not have effect on cellulose crystallinity so that only extended incubation in buffer resulted in such a dramatic increase in crystallinity index (additionally, both buffer and CBD pretreated samples were freeze-dryed before XRD analysis). The use of CBDs (up to 10 $\mu g.mg^{-1}$ at 40 $mg.mL^{-1}$ cellulose in a typical pretreatment step) resulted in a different trend, as it not only prevented the substrate from recrystallizing, but also reduced the initial crystallinity of cellulose. Avicel crystallinity reached 58% after incubation with a mixture of CBDs, while fibrous cellulose crystallinity reached 68%, a significant drop from the crystallinity indices obtained after incubation in buffer only. When cellulose was incubated with pure CBDs from cellobiohydrolase I Cel7A ($CBD_{Cel7A}$) over extensive periods of incubation (>48 h), an even higher reduction in crystallinity was obtained with Avicel (down to 53%, as shown in FIG. 14.

Though the difference between the spectra appears limited to one portion of the XRD patterns, the analytical method described above for interpretation of XRD data of cellulose allowed accurate determination of the crystallinity index. The drop in intensity observed at a Bragg angle of 22.5° ((200) plane) accounts for the overall reduction in crystallinity. Thus, CBDs from *Trichoderma reesei* (belonging to family I CBD, along with CBDs of cellulases from *Phanerochaete chrysosporium* or *Penicillium janthinellum*), though not catalytically active with cellulose, had a strong effect on the cellulose structure, as overall crystallinity was significantly reduced. Interestingly, the crystal plane (200) seems to be the only one affected by these changes as illustrated in FIG. 14. Overall, CBDs are responsible for splitting of intermolecular hydrogen bonds to such an extent that the cellulose crystallinity is noticeably reduced. While not wishing to be bound to any particular theory this most likely proceeds via a dynamic process (processive motion on cellulose surface required), which is still poorly understood.

Hydrolysis of CBD Pretreated Cellulose

Figure 15A:
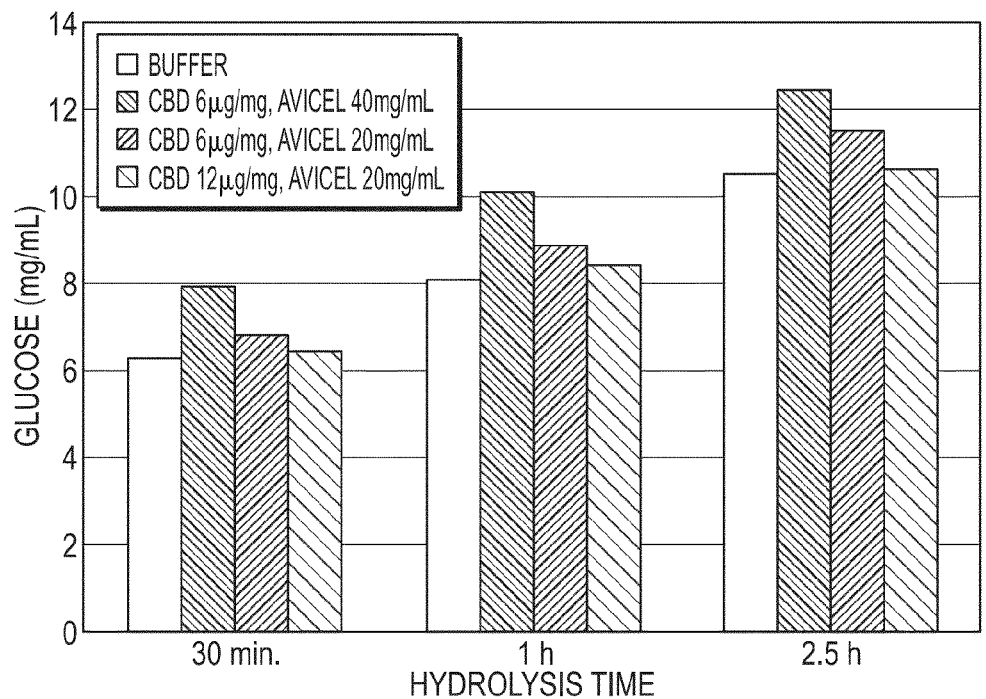
FIG. 15a shows the hydrolysis profile of Avicel after pretreatment with mixture of CBDs for 15 h at 42° C.

Cellulose incubated with CBDs for 15 h was hydrolyzed by adding cellulases (supplemented with β-glucosidase) to the pretreatment mixture (one-pot process). The pretreatment of Avicel at 40 $mg.mL^{-1}$ affected the conversion as shown in FIG. 15a, as the amount of sugar released from CBD pretreated samples (reduced crystallinity of 58%, Table 3) was 25% higher than that released from buffer pretreated samples (increased crystallinity of 65%, Table 3) after 30 min hydrolysis time (7.9 $mg.mL^{-1}$ vs. 6.3 $mg.mL^{-1}$ glucose resp.). Such an increase could potentially lead to a reduction in cost of the enzymatic process which is one of the major cost contributing factors in biofuel production from biomass.

Interestingly, no significant difference in rate compared to incubation in buffer only could be monitored at 20 $mg.mL^{-1}$ Avicel concentration when using the mixture of CBDs, even when the CBD concentration was increased to 12 $\mu g.mg^{-1}$ (FIG. 15a). Similar behavior was observed with fibrous cellulose: the incubation at 20 $mg.mL^{-1}$ FC concentration did not give a significant change in conversion compared to the incubation in buffer only (FIG. 15b), whereas 23% increase was obtained after incubation with CBDs at 40 $mg.mL^{-1}$ FC compared to buffer incubation (relating to 68% vs. 74% crystallinity resp., Table 3). The much slower rate obtained in the conversion of FC compared to Avicel can be explained in part by higher initial crystallinity (72% vs. 60% for untreated samples; however, surface area and particle size may also contribute).

It was observed that pretreatment with CBDs for 8 h instead of >15 h did not lead to significant change in the amount of glucose released during the hydrolysis step compared to the buffer incubated sample. Incubation with CBDs opens up new possibilities in cellulose pretreatment and avoids the use of harsh conditions (such as high temperature or acid concentration) or isolation of cellulose from the pretreatment mixture before hydrolysis with cellulases.

Figure 16:
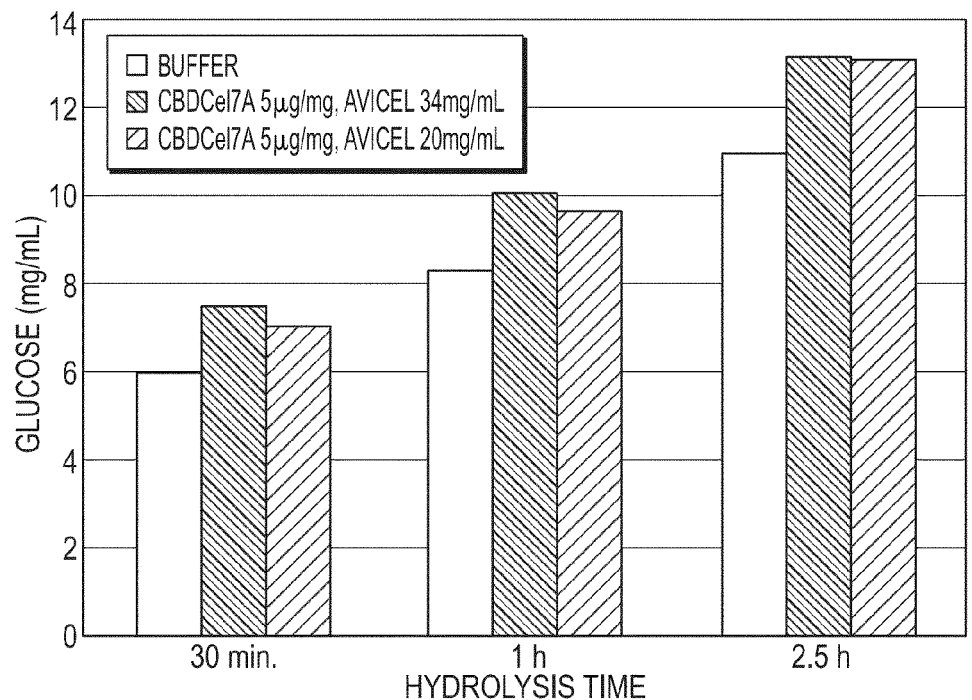
FIG. 16 shows the hydrolysis profile of Avicel after pretreatment with $CBD_{Cel7A}$ for 15 h at 42° C.

The exact amino acid sequence of family I CBDs seems less important for rate improvement: pretreatment with homogeneous $CBD_{Cel7A}$ yielded results comparable to those with a mixture of CBDs: increased rates i) after pretreatment at 42° C. (and also 37° C.) with $CBD_{Cel7A}$ compared to buffer only, ii) after 30 min hydrolysis (7.5 $mg.mL^{-1}$ vs. 6 $mg/mL^{-1}$): 25% increase in glucose concentration, and iii) under similar conditions (34 $mg.mL^{-1}$ Avicel concentration compared to 40 $mg.mL^{-1}$ with the mixture). However, pretreatment conducted at lower cellulose concentration (20 $mg.mL^{-1}$) also yielded faster conversion, as there was only a minor drop in rate in the case of the sample pretreated at 20 $mg.mL^{-1}$ (compared to 40 $mg.mL^{-1}$ as shown in FIG. 16).

While not wishing to be bound to any particular theory desorption of CBDs upon dilution performed prior to the hydrolysis might be responsible for the higher rates after pretreatment with a CBD mixture at 40 $mg.mL^{-1}$ (compared to no improvement at 20 $mg.mL^{-1}$). Such desorption would liberate binding spots for cellulases on the cellulose surface and thus increase overall hydrolysis rate. Though incubation in buffer led to an increase rather than decrease in overall cellulose crystallinity (Table 3), it provided hydration of the sample and a nearly two-fold increase in hydrolysis rate was observed compared to employing dry cellulose without pretreatment. Thus, the increase in rate obtained after pretreatment with CBDs may be a combination of hydration effect from the buffer and reduction in crystallinity from CBDs.

Figure 17:
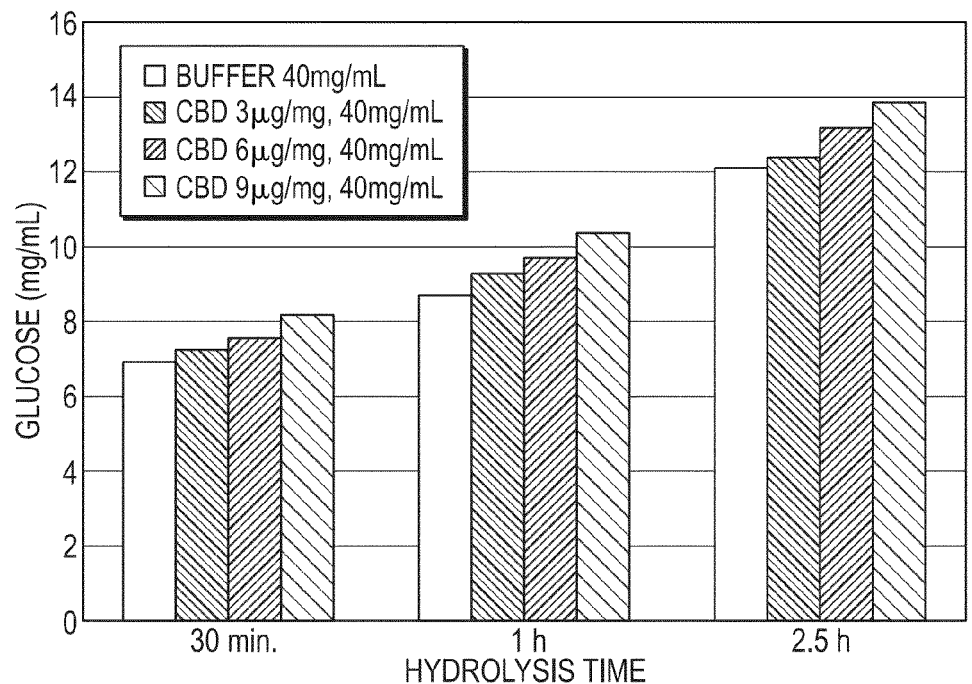
FIG. 17 shows effect of various CBD concentrations in the pretreatment step (15 h at 42° C.) on hydrolysis rate.

Increased CBD concentration during pretreatment led to enhanced production of glucose in the hydrolysis step as shown in FIG. 17. The present loading of 9 $\mu g.mg^{-1}$ is not saturating the surface since 150 $\mu g.mg^{-1}$ cellulase at a total loading of 1230 µg.mg$^{-1}$ bind to the cellulose surface as shown by Hall, et al, 2010. Cellulose crystallinity—a key predictor of the enzymatic hydrolysis rate. *Febs Journal*, 277, 1571-1582. And there was no saturation of Avicel employing up to 470 µg.mg$^{-1}$ CBD$_{Cel7A}$ (corresponding to 49 µg.mg bound CBD) as shown by Stahlberg, et al., 1991. A New Model for Enzymatic-Hydrolysis of Cellulose Based on the 2-Domain Structure of Cellobiohydrolase-I. *Bio-Technology*, 9, 286-290.

Figure 18:
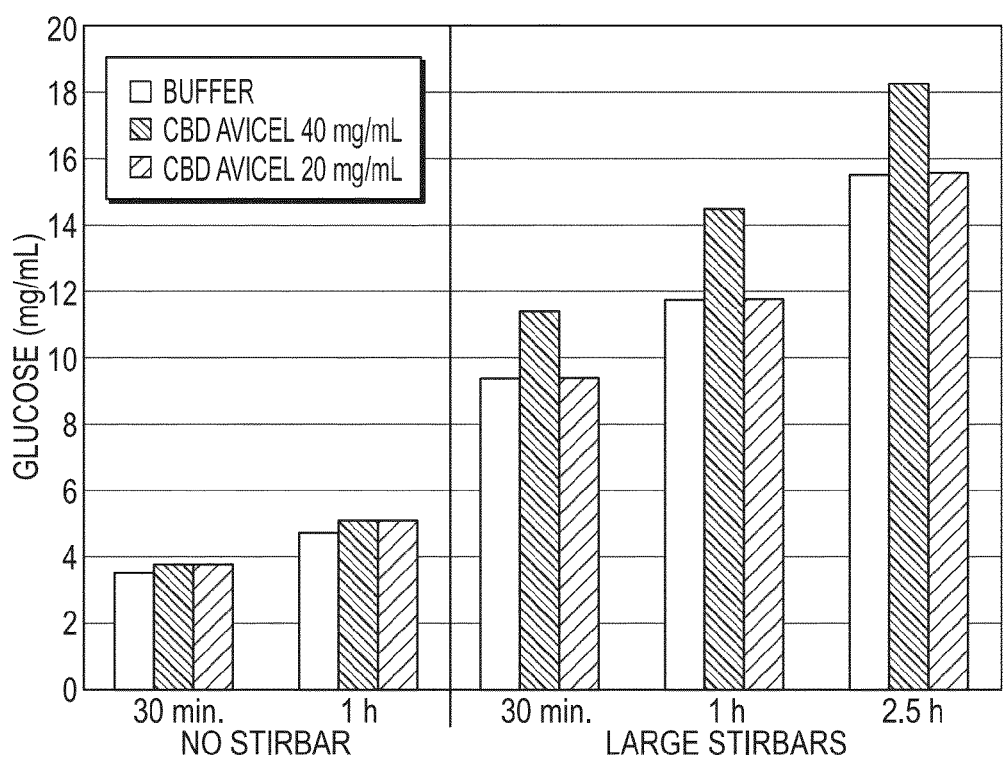
FIG. 18 shows the effect of stir bar during pretreatment of cellulose with CBDs on hydrolysis rates.

In the absence of stirring during pretreatment (but when shaking was still provided), overall reaction rates were 40% lower and incubation with CBDs surprisingly did not lead to an increase in glucose concentration as shown in FIG. 18. The use of stir bars 72% as large as the inner diameter of the vials resulted in up to 1.5 fold higher conversion levels in buffer, a positive effect of CBD incubation, but reduced reproducibility (most likely due to inhomogeneous stirring owing to geometric constraints in the reaction vial). Henceforth, stir bars of 55% of inner vial diameter were used. Likely, the lack of continual convection in the absence of stirring prevents lateral displacement of CBD molecules and thus limits their effectiveness, given the absence of catalytic events as a potential energy source for CBD movement along the cellulose surface.

Surprisingly and unexpectedly, preincubation of cellulose with CBDs lowered its index of crystallinity and resulted in higher glucose concentration in the subsequent hydrolysis reaction. Also, it was observed that simultaneous addition of CBDs to non-pretreated cellulose samples did not show any improvement in conversion levels. Thus, the use of CBDs in a pretreatment step rather than a one-step process combining addition of CBDs and full-length enzymes is surprisingly and unexpectedly effective. While not wishing to be bound to any particular theory, it may be that simultaneous addition of CBDs to the hydrolysis mixture prevents reduction of crystallinity by CBDs due to competitive binding with cellulases and/or hydrolysis of cellulose by cellulases.

Thermostability of CBDs

Similarly to the conditions used in the enzymatic hydrolysis of pretreated cellulose, pretreatment with CBDs was also performed at 50° C. After 15 h pretreatment at 50° C. and hydrolysis for 30 min, it was observed that conversion was only slightly lower than after pretreatment at 42° C. indicating that CBDs can be considered relatively thermostable. This observation was confirmed with binding experiments, where full-length cellulases were shown to bind similarly to Avicel after 15 h of incubation at 50° C., compared to storage at 4° C. as shown in Table 4 below.

resp.). It can thus be concluded that the observed thermolability of cellulases is mostly due to loss of catalytic activity rather than binding capacity, as pretreatment of cellulose with CBDs can be performed at 50° C.

CBD$_{Cel7A}$ is a small peptide (37 residues) and made up of an irregular triple-stranded antiparallel β-sheet as reported in, for example, Kraulis, et al., 1989. Determination of the 3-Dimensional Solution Structure of the C-Terminal Domain of Cellobiohydrolase-I from *Trichoderma-Reesei*—a Study Using Nuclear Magnetic-Resonance and Hybrid Distance Geometry Dynamical Simulated Annealing. *Biochemistry*, 28, 7241-7257. While not wishing to be bound to any particular theory it may be that the stability at higher temperatures may be at least in part due to its compact structure and/or the two disulfide bridges.

Conclusions

Cellulose-binding domains had impacted cellulose structure upon incubation. The crystallinity of different types of cellulose (microcrystalline and fibrous) was reduced after pretreatment with CBDs, rendering the substrates less recalcitrant to enzymatic hydrolysis, and an increase up to about 25% in glucose concentration during hydrolysis was obtained. These surprising and unexpected results show that cellulose binding domains can be used as a pretreatment method for cellulosic material. The inventive pretreatment employs biological molecules and relatively mild conditions instead of harsh chemicals and conditions. In addition, the inventive pretreatment may be used in a manner such that it does not require a change of solvent. Moreover, the binding capacity of CBDs is retained after extensive incubation at 50° C. while there is significant loss of catalytic activity.

Figure Legends

FIG. 1 SDS-PAGE of purified cel7A from *Trichoderma reesei* and cel7A catalytic domain after papain cleavage. Lane 1: ladder, lane 2: purified cel7A, lane 3: catalytic domain (CD) in concentrate after filtration through 30 kDa membrane (Coomassie staining).

FIG. 2 Enzymatic hydrolysis of Avicel after CBD treatment (numbers refer to cellulose sample from Table 2). Reactions were run as follows: 20 mg/ml Avicel, 50 mM NaOAc pH 5, 50° C. (#3 and 4 were used as freeze-dried powder, generated for X-ray diffraction analysis). All samples were incubated 1 h at 50° C. before addition of the enzyme to the reaction mixture.

FIG. 3. CBD incubation time effects (after reported time period, enzymes were added to the mixture of CBD and Avicel and hydrolysis was monitored by measuring glucose content, expressed as conversion %).

TABLE 4

Effect of 15 h incubation at 50° C. on catalytic activity of cellulases and catalytic domains (CDs) and binding of cellulases on Avicel (compared to standard storage at 4° C.).

| Incubation temperature | Activity (Glucose concentration in mg · mL$^{-1}$) | | Binding capacity (bound cellulases µg · mg$^{-1}$) |
|---|---|---|---|
| | Cellulase cocktail | CDs | |
| 4° C. | After 6 h: 5.6 | After 6 h: 1.2 | 37.3 (total added 90 µg · mg$^{-1}$) |
| | After 22 h: 8.2 | After 22 h: 2.2 | 38.4 (total added 150 µg · mg$^{-1}$) |
| 50° C. | After 6 h: 3.2 | After 6 h: 0.5 | 41.4 (total added 90 µg · mg$^{-1}$) |
| | After 22 h: 3.6 | After 22 h: 0.7 | 44.0 (total added 150 µg · mg$^{-1}$) |

The activity of cellulases, however, was affected by the same incubation period at 50° C. (1.8 fold decrease after 6 h hydrolysis, up to 2.3 after 22 h). The catalytic activity of CDs was even more reduced after incubation at 50° C. (2.4 and 3.1 fold decrease in glucose concentration after 6 h and 22 h FIG. 4. Effect of buffer incubation on hydrolysis rate compared to CBD incubation (13 h). Avicel was incubated in CBD solution or in buffer for 13 h (also 1 h in buffer). Cellulases were then added to the reaction mixture and glucose content was monitored for up to 2.5 h.

FIG. 5. Effect of buffer incubation time on hydrolysis rates. Avicel was incubated in buffer over various periods of time. Cellulases were then added to the reaction mixture and glucose content was monitored for up to 4 h.

FIG. 6. CBD concentration optimization experiment (Vr represents the starting concentration). Graph b consists of the same data as graph a but for the lines connecting the data points.

FIG. 7. The hydrolysis for various CBD treatment times.

FIG. 8. The effect of various concentrations of CDB.

Figure 9:
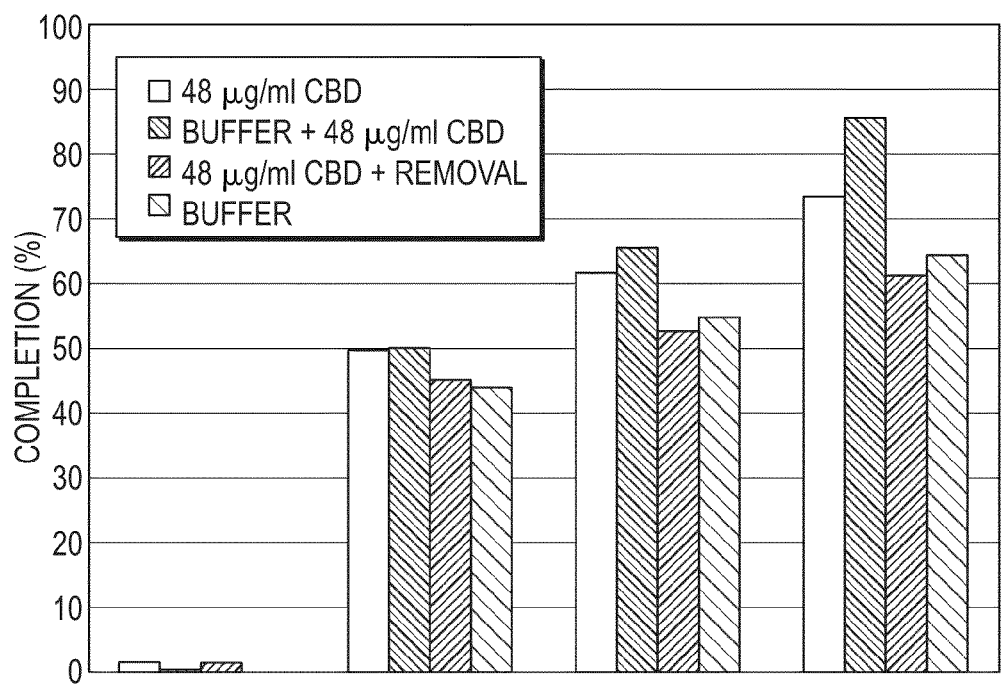
FIG. 9 shows the effect of sequential addition and CBD removal.

FIG. 9. The effect of sequential addition and CBD removal.

FIG. 10. The effect of a 45° C. treatment.

FIG. 11. The effect of a 50° C. treatment.

FIG. 12. Production of reducing ends from switchgrass using cellulases and β-glucosidase after treatment with CBD, treatment with buffer, no treatment with simultaneous addition of CBD and no treatment (dry sample).

FIG. 13. SDS-PAGE before and after papain cleavage of cellulases. Lane 1: ladder, lane 2: cellulase cocktail from *Trichoderma reesei* after filtration through 30 kDa membrane, lane 3: catalytic domains (CDs) of cellulases, lane 4: purified Cel7A after anion-exchange chromatography, lane 5: CD of purified Cel7A, lane 6: ladder, lanes 7 and 8: higher loading of cellulase cocktail from *Trichoderma reesei* after filtration through 30 kDa and corresponding CDs, lane 9: purified Cel7A (lower loading).

FIG. 14. XRD spectra for Avicel samples treated with $CBD_{Cel7A}$ (cellulose-binding domain from purified Cel7A), $CD_{Cel7A}$ (catalytic domain) or buffer. The spectral data have been normalized according to Bansal et al., 2010. Multivariate statistical analysis of X-ray data from cellulose: A new method to determine degree of crystallinity and predict hydrolysis rates. *Bioresource Technology*, 101, 4461-4471. 1 and 2 refer to duplicated experiments.

FIG. 15a. Hydrolysis profile of Avicel after pretreatment with mixture of CBDs for 15 h at 42° C. (the hydrolysis was run at 50° C. and 20 mg.mL$^{-1}$ cellulose. The cellulose concentration refers to the actual concentration during pretreatment).

Figure 15B:
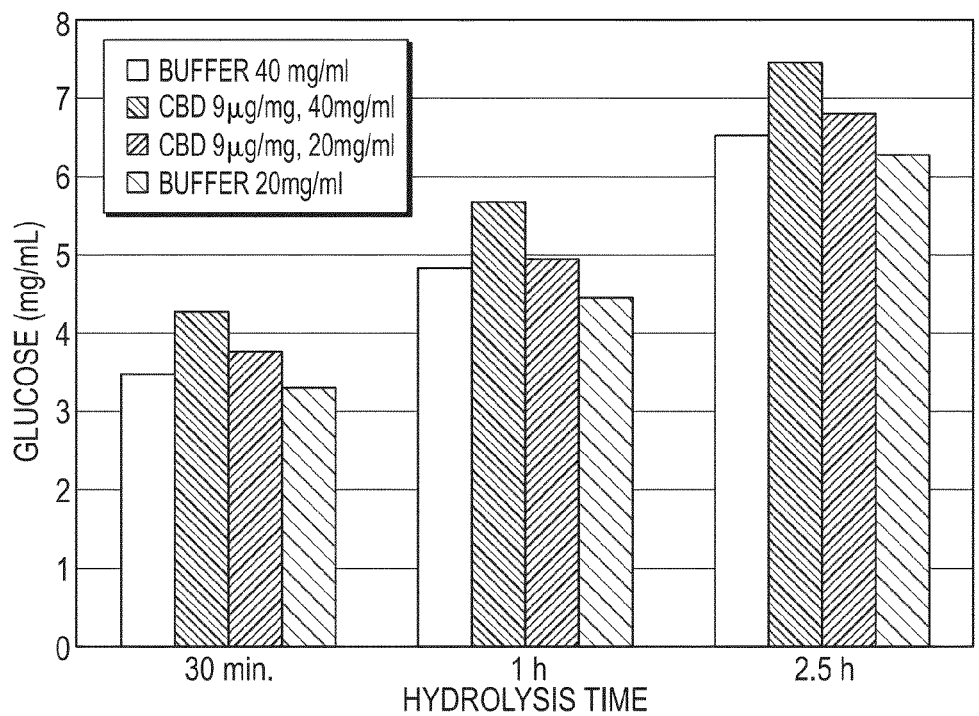
FIG. 15b shows the hydrolysis profile of fibrous cellulose (FC) after pretreatment with mixture of CBDs for 15 h at 42° C.

FIG. 15b. Hydrolysis profile of fibrous cellulose (FC) after pretreatment with mixture of CBDs for 15 h at 42° C. (the hydrolysis was run at 50° C. and 20 mg.mL$^{-1}$ cellulose. The cellulose concentration refers to the actual concentration during pretreatment).

FIG. 16. Hydrolysis profile of Avicel after pretreatment with $CBD_{Cel7A}$ for 15 h at 42° C. (the hydrolysis was run at 50° C. and 20 mg.mL$^{-1}$ cellulose. The cellulose concentration refers to the actual concentration during pretreatment).

FIG. 17. Effect of various CBD concentrations in the pretreatment step (15 h at 42° C.) on hydrolysis rate (the hydrolysis was run at 50° C. and 20 mg.mL$^{-1}$ cellulose. The cellulose concentration refers to the actual concentration during pretreatment).

FIG. 18. Effect of stir bar during pretreatment of cellulose with CBDs on hydrolysis rates. The pretreatment was run at 42° C. for 15 h without stir bar (10 μg.mg$^{-1}$), or with large stir bars (7.5 μg.mg$^{-1}$). The hydrolysis was run at 50° C. and 20 mg.mL$^{-1}$ cellulose concentration.

Figure 19:
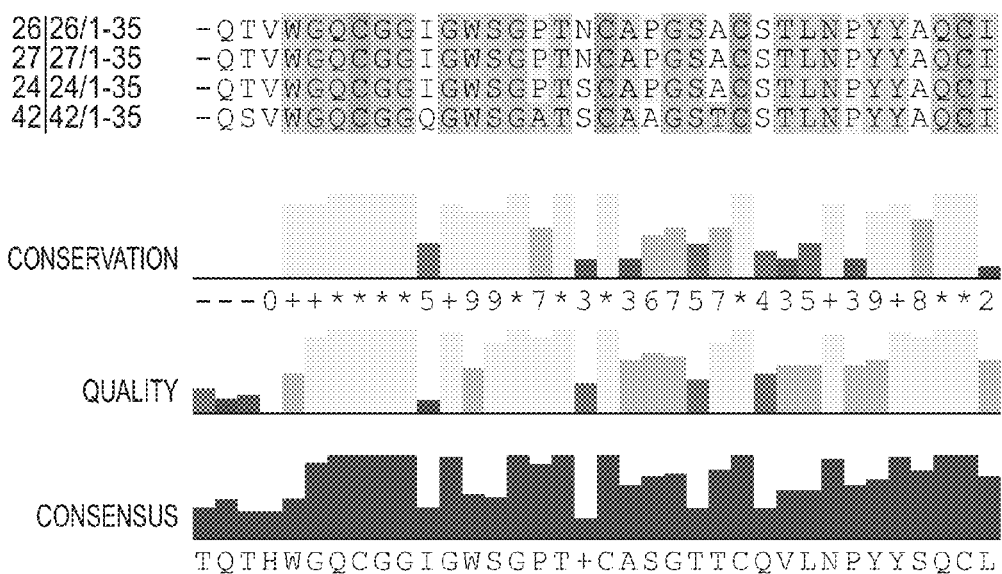
FIG. 19 shows amino acid sequences of various CBDs that may be useful in the present inventions.

FIG. 19. Amino acid sequences of the CBD of major organisms. The sequences of FIG. 19 were identified via a BLAST search (http://blast.ncbi.nlm.nih.gov/Blast.cgi#) (Altschul SF, Gish W, Miller W, Myers E W, Lipman D J: Basic Local Alignment Search Tool. *Journal of Molecular Biology* 1990, 215:403-410). The sequences were aligned using clustalW (Thompson J D, Higgins D G, Gibson T J: CLUSTAL W: improving the sensitivity of progressive multiple sequence alignment through sequence weighting, position-specific gap penalties and weight matrix choice. *Nucleic Acids Res* 1994, 22(22):4673-4680). The names of enzymes and species, of which the sequences in FIG. 19 are a part of (according to the number in the alignment xx| where xx denotes the number; e.g., the *Trichoderma reesei* Cel7A CBD sequence is designated 1|1/1-36 outlined in FIG. 19 is number 1 in Table 5 below).

TABLE 5

| Number | Enzyme (species) |
|---|---|
| 1 | Cel7A [*Trichoderma reesei*] |
| 2 | cellobiohydrolase I [*Trichoderma viride*] |
| 3 | cellubiohydrolase I [*Trichoderma* sp. XST1] |
| 4 | bifunctional chitosanase-cellulase [*Trichoderma viride*] |
| 5 | Cip1 [*Hypocrea jecorina*] |
| 6 | cellobiohydrolase I [*Hypocrea virens*] |
| 7 | cellobiohydrolase [*Hypocrea lixii*] |
| 8 | cellobiohydrolase I [*Neolentinus lepideus*] |
| 9 | exocellobiohydrolase [*Phanerochaete chrysosporium*] |
| 10 | endo-1,4-xylanase D [*Penicillium funiculosum*] |
| 11 | endoglucanase [*Aspergillus fumigatus* Af293] |
| 12 | xylanase/cellobiohydrolase [*Penicillium funiculosum*] |
| 13 | cellobiohydrolase I [*Penicillium occitanis*] |
| 14 | glycosyl hydrolase family 45 protein [*Neosartorya fischeri* NRRL 181] |
| 15 | cellulose binding protein [*Phanerochaete chrysosporium*] |
| 16 | CBHI [*Volvariella volvacea*] |
| 17 | endo-1,4-beta-xylanase [*Aspergillus fumigatus* Af293] |
| 18 | cellulose binding iron reductase [*Coprinopsis cinerea* okayama7#130] |
| 19 | Acetyl xylan esterase [*Hypocrea jecorina*] |
| 20 | cellulase [*Irpex lacteus*] |
| 21 | endoglucanase IV [*Trichoderma viride*] |
| 22 | endoglucanase IV [*Trichoderma* sp. SSL] |
| 23 | endoglucanase 1 [*Penicillium echinulatum*] |
| 24 | endoglucanase II [*Trichoderma viride*] |
| 25 | endoglucanase III [*Trichoderma viride*] |
| 26 | endoglucanase III [*Hypocrea jecorina*] |
| 27 | endoglucanase II [*Hypocrea jecorina*] |
| 28 | glycoside hydrolase family 5 [*Nectria haematococca*] |
| 29 | glycosyl hydrolase family 61 [*Glomerella graminicola* M1.001] |
| 30 | cellulase [*Irpex lacteus*] |
| 31 | endo-1,4-beta-xylanase C precursor [*Phanerochaete chrysosporium*] |
| 32 | endoglucanase I [*Penicillium oxalicum*] |
| 33 | endoglucanase I [*Penicillium decumbens*] |
| 34 | cellulose binding protein [*Talaromyces emersonii*] |
| 35 | cellulose-binding beta-glucosidase [*Phanerochaete chrysosporium*] |
| 36 | Acetyl xylan esterase [*Aspergillus fumigatus* Af293] |
| 37 | glycosyl hydrolase family 62 protein [*Coprinopsis cinerea* okayama7#130] |
| 38 | Family 61 endoglucanase [*Phanerochaete chrysosporium*] |
| 39 | Fungal cellulose binding domain protein [*Aspergillus clavatus* NRRL 1] |
| 40 | cellulase CEL7A [*Lentinula edodes*] |
| 41 | exoglucanase [*Verticillium albo-atrum* VaMs.102] |
| 42 | cellobiohydrolase II [*Acremonium cellulolyticus* Y-94] |
| 43 | glycosyl hydrolase family 7 protein [*Neosartorya fischeri* NRRL 181] |
| 44 | cellulase CEL6B [*Lentinula edodes*] |

The claimed subject matter is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety to the extent that they are not inconsistent and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A pre-treatment process for treating a feedstock comprising holocellulose wherein the process comprises:
    a) mixing the feedstock with a solution comprising cellulose binding domains to form a mixture; and
    b) subjecting the mixture to conditions sufficient to reduce the crystallinity of holocellulose prior to hydrolysis.

2. The process of claim 1 wherein the cellulose binding domains are derived from cellobiohydrolase I (cel7A) or cellobiohydrolase II (cel6A).

3. The process of claim 1 wherein the cellulose binding domains are derived from cellobiohydrolase I (cel7A) produced by *Trichoderma reesei*.

4. The process of claim 1 wherein the mixture is subjected to a temperature of greater than about 30° C. for a time sufficient to reduce the crystallinity of holocellulose.

5. The process of claim 1 wherein the mixture is subjected to a temperature of greater than about 35° C. for a time sufficient to reduce the crystallinity of holocellulose.

6. The process of claim 1 wherein the mixture is subjected to a temperature of from about 30° C. up to about 50° C. for a time sufficient to reduce the crystallinity of holocellulose.

7. The process of claim 1 wherein the mixture is subjected to a temperature of from about 35° C. up to about 45° C. for a time sufficient to reduce the crystallinity of holocellulose.

8. The process of claim 1 wherein the mixture is subjected to increased temperature for at least about 8 hours.

9. The process of claim 1 wherein the mixture is subjected to increased temperature for at least about 10 hours.

10. The process of claim 1 wherein the mixture is subjected to increased temperature for at least about 12 hours.

11. The process of claim 1 wherein the mixture is subjected to stirring such that substantially all solids are suspended.

12. The process of claim 1 wherein the solution comprising cellulose binding domains has a concentration of from about 5 to about 55 μg/ml.

13. The process of claim 1 wherein the solution comprising cellulose binding domains further comprises a suitable buffer selected from the group consisting of lower alkyl acid salts and lower alkyl acid esters.

14. The process of claim 1 wherein the solution comprising cellulose binding domains further comprises a suitable buffer wherein the solution has a pH of from about 4.5 to about 5.5.

15. The process of claim 1 wherein the solution comprising cellulose binding domains further comprises a suitable buffer comprising sodium acetate wherein the solution has a pH of from about 4.5 to about 5.5.

16. The process of claim 1 wherein the solution comprising cellulose binding domains further comprises a 25 to 75 mM sodium acetate buffer wherein the solution has a pH of about 5.

17. The process of claim 1 which further comprises hydrolyzing the product of step 1b in claim 1 to produce a composition comprising at least one fermentable sugar.

18. The process of claim 17 wherein the fermentable sugar in said composition is at least about 10% more than a comparable process which does not employ cellulose binding domains.

19. The process of claim 1 wherein the ratio of cellulose binding domains to catalytic domain is greater than 1:1.

20. The process of claim 1 wherein the ratio of cellulose binding domains to catalytic domain is greater than 5:1.

21. A pre-treatment composition suitable for reducing the crystallinity of cellulose prior to hydrolysis, said composition comprising cellulose, a suitable concentration of a solution comprising cellulose binding domains, and a suitable buffer selected from the group consisting of lower alkyl acid salts and lower alkyl acid esters.

22. The composition of claim 21 wherein the cellulose binding domains are derived from cellobiohydrolase I (cel7A) produced by *Trichoderma reesei*.

23. The composition of claim 21 wherein the solution comprising cellulose binding domains has a concentration of from about 5 to about 55 μg/ml wherein the buffer comprises a 25 to 75 mM sodium acetate buffer and wherein the solution has a pH of about 5.

24. The composition of claim 21 wherein the solution comprising cellulose binding domains has a ratio of cellulose binding domains to catalytic domain which is greater than 5:1.

* * * * *

SEQUENCE LISTING

<160> NUMBER OF SEQ ID NOS: 44

<210> SEQ ID NO 1
<211> LENGTH: 36
<212> TYPE: PRT
<213> ORGANISM: Trichoderma reesei
<220> FEATURE:
<223> OTHER INFORMATION: part of sequence from enzyme Cel7A

<400> SEQUENCE: 1

Thr Gln Ser His Tyr Gly Gln Cys Gly Gly Ile Gly Tyr Ser Gly Pro
 1               5                  10                  15

Thr Val Cys Ala Ser Gly Thr Thr Cys Gln Val Leu Asn Pro Tyr Tyr
            20                  25                  30

Ser Gln Cys Leu
        35

<210> SEQ ID NO 2
<211> LENGTH: 36
<212> TYPE: PRT
<213> ORGANISM: Trichoderma viride
<220> FEATURE:
<223> OTHER INFORMATION: part of sequence from cellobiohydrolase I

<400> SEQUENCE: 2

Thr Gln Ser His Tyr Gly Gln Cys Gly Gly Ile Gly Tyr Ser Gly Pro
 1               5                  10                  15

Thr Val Cys Ala Ser Gly Thr Thr Cys Gln Val Leu Asn Pro Tyr Tyr
            20                  25                  30

Ser Gln Cys Leu
        35

<210> SEQ ID NO 3
<211> LENGTH: 36
<212> TYPE: PRT
<213> ORGANISM: Trichoderma sp. XST1
<220> FEATURE:
<223> OTHER INFORMATION: part of sequence from cellubiohydrolase I

<400> SEQUENCE: 3

Thr Gln Thr His Tyr Gly Gln Cys Gly Gly Ile Gly Tyr Ser Gly Pro
 1               5                  10                  15

Thr Val Cys Ala Ser Gly Thr Thr Cys Gln Val Leu Asn Glu Tyr Tyr
            20                  25                  30

Ser Gln Cys Leu
        35

<210> SEQ ID NO 4
<211> LENGTH: 36
<212> TYPE: PRT
<213> ORGANISM: Trichoderma viride
<220> FEATURE:
<223> OTHER INFORMATION: part of sequence from bifunctional
      chitosanase-cellulase

<400> SEQUENCE: 4

Thr Gln Thr His Tyr Gly Gln Cys Gly Gly Ile Gly Tyr Ser Gly Pro
 1               5                  10                  15

Thr Val Cys Ala Ser Gly Thr Thr Cys Gln Val Leu Asn Glu Tyr Tyr
            20                  25                  30

Ser Gln Cys Leu
        35

```
<210> SEQ ID NO 5
<211> LENGTH: 33
<212> TYPE: PRT
<213> ORGANISM: Hypocrea jecorina
<220> FEATURE:
<223> OTHER INFORMATION: part of sequence from Cip1

<400> SEQUENCE: 5

His Tyr Gly Gln Cys Gly Gly Ile Gly Tyr Ser Gly Pro Thr Val Cys
 1               5                  10                  15

Ala Ser Gly Thr Thr Cys Gln Val Leu Asn Pro Tyr Tyr Ser Gln Cys
             20                  25                  30

Leu

<210> SEQ ID NO 6
<211> LENGTH: 36
<212> TYPE: PRT
<213> ORGANISM: Hypocrea virens
<220> FEATURE:
<223> OTHER INFORMATION: part of sequence from cellobiohydrolase I

<400> SEQUENCE: 6

Thr Gln Thr His Tyr Gly Gln Cys Gly Gly Ile Gly Tyr Ser Gly Pro
 1               5                  10                  15

Thr Gln Cys Val Ser Gly Thr Thr Cys Gln Val Leu Asn Pro Phe Tyr
             20                  25                  30

Ser Gln Cys Leu
         35

<210> SEQ ID NO 7
<211> LENGTH: 36
<212> TYPE: PRT
<213> ORGANISM: Hypocrea lixii
<220> FEATURE:
<223> OTHER INFORMATION: part of sequence from cellobiohydrolase

<400> SEQUENCE: 7

Thr Gln Thr His Tyr Gly Gln Cys Gly Gly Thr Gly Trp Thr Gly Pro
 1               5                  10                  15

Thr Arg Cys Ala Ser Gly Phe Thr Cys Gln Val Leu Asn Pro Phe Tyr
             20                  25                  30

Ser Gln Cys Leu
         35

<210> SEQ ID NO 8
<211> LENGTH: 36
<212> TYPE: PRT
<213> ORGANISM: Neolentinus lepideus
<220> FEATURE:
<223> OTHER INFORMATION: part of sequence from tcellobiohydrolase I

<400> SEQUENCE: 8

Thr Gln Thr Lys Tyr Gly Gln Cys Gly Gly Gln Gly Tyr Ser Gly Pro
 1               5                  10                  15

Thr Val Cys Ala Ser Gly Ser Thr Cys Gln Thr Ser Asn Pro Tyr Tyr
             20                  25                  30

Ser Gln Cys Leu
         35

<210> SEQ ID NO 9
<211> LENGTH: 34
<212> TYPE: PRT
```

```
<213> ORGANISM: Phanerochaete chrysosporium
<220> FEATURE:
<223> OTHER INFORMATION: part of sequence from exocellobiohydrolase

<400> SEQUENCE: 9

Ser Glu Trp Gly Gln Cys Gly Gly Ile Gly Trp Thr Gly Pro Thr Thr
1               5                   10                  15

Cys Val Ser Gly Thr Thr Cys Thr Val Leu Asn Pro Tyr Tyr Ser Gln
            20                  25                  30

Cys Leu

<210> SEQ ID NO 10
<211> LENGTH: 33
<212> TYPE: PRT
<213> ORGANISM: Penicillium funiculosum
<220> FEATURE:
<223> OTHER INFORMATION: part of sequence from endo-1,4-xylanase D

<400> SEQUENCE: 10

His Trp Gly Gln Cys Gly Gly Ile Gly Trp Ser Gly Pro Thr Ile Cys
1               5                   10                  15

Val Ser Pro Tyr Thr Cys Gln Val Leu Asn Pro Tyr Tyr Ser Gln Cys
            20                  25                  30

Leu

<210> SEQ ID NO 11
<211> LENGTH: 36
<212> TYPE: PRT
<213> ORGANISM: Aspergillus fumigatus Af293
<220> FEATURE:
<223> OTHER INFORMATION: part of sequence from endoglucanase

<400> SEQUENCE: 11

Thr Gln Thr His Tyr Gly Gln Cys Gly Gly Gln Gly Trp Thr Gly Pro
1               5                   10                  15

Thr Ala Cys Ala Ser Pro Tyr Thr Cys Gln Val Leu Asn Pro Trp Tyr
            20                  25                  30

Ser Gln Cys Leu
        35

<210> SEQ ID NO 12
<211> LENGTH: 34
<212> TYPE: PRT
<213> ORGANISM: Penicillium funiculosum
<220> FEATURE:
<223> OTHER INFORMATION: part of sequence from
      xylanase/cellobiohydrolase

<400> SEQUENCE: 12

Ala His Trp Gly Gln Cys Gly Gly Gln Gly Trp Thr Gly Pro Thr Thr
1               5                   10                  15

Cys Ala Ser Gly Thr Thr Cys Thr Val Val Asn Pro Tyr Tyr Ser Gln
            20                  25                  30

Cys Leu

<210> SEQ ID NO 13
<211> LENGTH: 33
<212> TYPE: PRT
<213> ORGANISM: Penicillium occitanis
<220> FEATURE:
<223> OTHER INFORMATION: part of sequence from cellobiohydrolase I

<400> SEQUENCE: 13
```

```
His Trp Gly Gln Cys Gly Gly Gln Gly Trp Thr Gly Pro Thr Thr Cys
 1               5                  10                  15

Val Ser Gly Thr Thr Cys Thr Val Val Asn Pro Tyr Tyr Ser Gln Cys
                20                  25                  30

Leu

<210> SEQ ID NO 14
<211> LENGTH: 36
<212> TYPE: PRT
<213> ORGANISM: Neosartorya fischeri NRRL 181
<220> FEATURE:
<223> OTHER INFORMATION: part of sequence from glycosyl hydrolase family
      45 protein

<400> SEQUENCE: 14

Thr Gln Thr Leu Tyr Gly Gln Cys Gly Gly Ser Gly Trp Thr Gly Pro
 1               5                  10                  15

Thr Ala Cys Ala Ser Gly Ala Thr Cys Lys Val Leu Asn Ser Tyr Tyr
                20                  25                  30

Ser Gln Cys Leu
            35

<210> SEQ ID NO 15
<211> LENGTH: 31
<212> TYPE: PRT
<213> ORGANISM: Phanerochaete chrysosporium
<220> FEATURE:
<223> OTHER INFORMATION: part of sequence from cellulose binding protein

<400> SEQUENCE: 15

Trp Gly Gln Cys Gly Gly Ile Gly Tyr Thr Gly Pro Thr Val Cys Ala
 1               5                  10                  15

Ser Gly Phe Thr Cys His Val Leu Asn Pro Tyr Tyr Ser Gln Cys
                20                  25                  30

<210> SEQ ID NO 16
<211> LENGTH: 30
<212> TYPE: PRT
<213> ORGANISM: Volvariella volvacea
<220> FEATURE:
<223> OTHER INFORMATION: part of sequence from CBHI

<400> SEQUENCE: 16

Gly Gln Cys Gly Gly Ile Gly Tyr Thr Gly Pro Thr Thr Cys Ala Ser
 1               5                  10                  15

Pro Thr Cys His Val Leu Asn Pro Tyr Tyr Ser Gln Cys
                20                  25                  30

<210> SEQ ID NO 17
<211> LENGTH: 33
<212> TYPE: PRT
<213> ORGANISM: Aspergillus fumigatus Af293
<220> FEATURE:
<223> OTHER INFORMATION: part of sequence from endo-1,4-beta-xylanase

<400> SEQUENCE: 17

Lys Trp Gly Gln Cys Gly Gly Ile Gly Trp Thr Gly Pro Thr Thr Cys
 1               5                  10                  15

Val Ser Gly Thr Thr Cys Gln Lys Leu Asn Asp Trp Tyr Ser Gln Cys
                20                  25                  30

Leu

<210> SEQ ID NO 18
```

-continued

```
<211> LENGTH: 36
<212> TYPE: PRT
<213> ORGANISM: Coprinopsis cinerea okayama7#130
<220> FEATURE:
<223> OTHER INFORMATION: part of sequence from cellulose binding iron
      reductase

<400> SEQUENCE: 18

Thr Gln Thr Ile Tyr Gly Gln Cys Gly Gly Thr Gly Tyr Ser Gly Pro
1               5                   10                  15

Thr Val Cys Ala Gly Gly Ser Arg Cys Lys Gln Val Asn Pro His Phe
            20                  25                  30

Ser Gln Cys Leu
        35

<210> SEQ ID NO 19
<211> LENGTH: 36
<212> TYPE: PRT
<213> ORGANISM: Hypocrea jecorina
<220> FEATURE:
<223> OTHER INFORMATION: part of sequence from Acetyl xylan esterase

<400> SEQUENCE: 19

Thr Gln Thr His Trp Gly Gln Cys Gly Gly Gln Gly Trp Thr Gly Pro
1               5                   10                  15

Thr Gln Cys Glu Ser Gly Thr Thr Cys Gln Val Ile Ser Gln Trp Tyr
            20                  25                  30

Ser Gln Cys Leu
        35

<210> SEQ ID NO 20
<211> LENGTH: 35
<212> TYPE: PRT
<213> ORGANISM: Irpex lacteus
<220> FEATURE:
<223> OTHER INFORMATION: part of sequence from cellulase

<400> SEQUENCE: 20

Thr Ala Ala Gln Trp Ala Gln Cys Gly Gly Met Gly Phe Thr Gly Pro
1               5                   10                  15

Thr Val Cys Ala Ser Pro Phe Thr Cys His Val Leu Asn Pro Tyr Tyr
            20                  25                  30

Ser Gln Cys
        35

<210> SEQ ID NO 21
<211> LENGTH: 36
<212> TYPE: PRT
<213> ORGANISM: Trichoderma viride
<220> FEATURE:
<223> OTHER INFORMATION: part of sequence from endoglucanase IV

<400> SEQUENCE: 21

Thr Gln Thr Leu Tyr Gly Gln Cys Gly Gly Ser Gly Tyr Ser Gly Pro
1               5                   10                  15

Thr Arg Cys Ala Pro Pro Ala Thr Cys Ser Thr Leu Asn Pro Tyr Tyr
            20                  25                  30

Ala Gln Cys Leu
        35

<210> SEQ ID NO 22
<211> LENGTH: 36
<212> TYPE: PRT
<213> ORGANISM: Trichoderma sp. SSL
```

<220> FEATURE:
<223> OTHER INFORMATION: part of sequence from endoglucanase IV

<400> SEQUENCE: 22

Thr Gln Thr Leu Tyr Gly Gln Cys Gly Gly Ser Gly Tyr Ser Gly Pro
1               5                   10                  15

Thr Arg Cys Ala Pro Pro Ala Thr Cys Ser Thr Leu Asn Pro Tyr Tyr
                20                  25                  30

Ala Gln Cys Leu
        35

<210> SEQ ID NO 23
<211> LENGTH: 33
<212> TYPE: PRT
<213> ORGANISM: Penicillium echinulatum
<220> FEATURE:
<223> OTHER INFORMATION: part of sequence from endoglucanase 1

<400> SEQUENCE: 23

His Trp Ala Gln Cys Gly Gly Val Gly Tyr Ser Gly Pro Thr Ala Cys
1               5                   10                  15

Ala Ser Pro Tyr Thr Cys Lys Val Gln Asn Asp Tyr Tyr Ser Gln Cys
                20                  25                  30

Leu

<210> SEQ ID NO 24
<211> LENGTH: 35
<212> TYPE: PRT
<213> ORGANISM: Trichoderma viride
<220> FEATURE:
<223> OTHER INFORMATION: part of sequence from endoglucanase II

<400> SEQUENCE: 24

Gln Thr Val Trp Gly Gln Cys Gly Gly Ile Gly Trp Ser Gly Pro Thr
1               5                   10                  15

Ser Cys Ala Pro Gly Ser Ala Cys Ser Thr Leu Asn Pro Tyr Tyr Ala
                20                  25                  30

Gln Cys Ile
        35

<210> SEQ ID NO 25
<211> LENGTH: 35
<212> TYPE: PRT
<213> ORGANISM: Trichoderma viride
<220> FEATURE:
<223> OTHER INFORMATION: part of sequence from endoglucanase III

<400> SEQUENCE: 25

Gln Thr Val Trp Gly Gln Cys Gly Gly Ile Gly Trp Ser Gly Pro Thr
1               5                   10                  15

Asn Cys Ala Pro Gly Ser Ala Cys Ser Thr Leu Asn Pro Tyr Tyr Ala
                20                  25                  30

Gln Cys Ile
        35

<210> SEQ ID NO 26
<211> LENGTH: 35
<212> TYPE: PRT
<213> ORGANISM: Hypocrea jecorina
<220> FEATURE:
<223> OTHER INFORMATION: part of sequence from endoglucanase III

<400> SEQUENCE: 26

```
Gln Thr Val Trp Gly Gln Cys Gly Gly Ile Gly Trp Ser Gly Pro Thr
 1               5                  10                  15

Asn Cys Ala Pro Gly Ser Ala Cys Ser Thr Leu Asn Pro Tyr Tyr Ala
            20                  25                  30

Gln Cys Ile
        35

<210> SEQ ID NO 27
<211> LENGTH: 35
<212> TYPE: PRT
<213> ORGANISM: Hypocrea jecorina
<220> FEATURE:
<223> OTHER INFORMATION: part of sequence from endoglucanase II

<400> SEQUENCE: 27

Gln Thr Val Trp Gly Gln Cys Gly Gly Ile Gly Trp Ser Gly Pro Thr
 1               5                  10                  15

Asn Cys Ala Pro Gly Ser Ala Cys Ser Thr Leu Asn Pro Tyr Tyr Ala
            20                  25                  30

Gln Cys Ile
        35

<210> SEQ ID NO 28
<211> LENGTH: 35
<212> TYPE: PRT
<213> ORGANISM: Nectria haematococca
<220> FEATURE:
<223> OTHER INFORMATION: part of sequence from glycoside hydrolase
      family 5

<400> SEQUENCE: 28

Gln Val Lys Tyr Gly Gln Cys Gly Gly Ser Gly Trp Thr Gly Pro Thr
 1               5                  10                  15

Leu Cys Glu Ser Gly Ser Thr Cys Gln Val Gln Asn Gln Trp Tyr Ser
            20                  25                  30

Gln Cys Leu
        35

<210> SEQ ID NO 29
<211> LENGTH: 36
<212> TYPE: PRT
<213> ORGANISM: Glomerella graminicola M1.001
<220> FEATURE:
<223> OTHER INFORMATION: part of sequence from glycosyl hydrolase family
      61

<400> SEQUENCE: 29

Thr Val Pro Lys Tyr Gly Gln Cys Gly Gly Gln Gly Trp Ser Gly Pro
 1               5                  10                  15

Thr Thr Cys Ala Ser Gly Ser Thr Cys Gln Ala Leu Asn Asp Phe Tyr
            20                  25                  30

Ser Gln Cys Val
        35

<210> SEQ ID NO 30
<211> LENGTH: 35
<212> TYPE: PRT
<213> ORGANISM: Irpex lacteus
<220> FEATURE:
<223> OTHER INFORMATION: part of sequence from cellulase

<400> SEQUENCE: 30

Thr Val Ala Gln Trp Gly Gln Cys Gly Gly Thr Gly Phe Thr Gly Pro
 1               5                  10                  15
```

-continued

```
Thr Val Cys Ala Ser Pro Phe Thr Cys His Val Val Asn Pro Tyr Tyr
            20                  25                  30

Ser Gln Cys
        35

<210> SEQ ID NO 31
<211> LENGTH: 33
<212> TYPE: PRT
<213> ORGANISM: Phanerochaete chrysosporium
<220> FEATURE:
<223> OTHER INFORMATION: part of sequence from endo-1,4-beta-xylanase C
      precursor

<400> SEQUENCE: 31

Glu Trp Gly Gln Cys Gly Gly Ile Gly Trp Thr Gly Pro Thr Thr Cys
1               5                   10                  15

Val Ala Gly Thr Thr Cys Val Glu Ser Asn Pro Tyr Tyr Ser Gln Cys
            20                  25                  30

Leu

<210> SEQ ID NO 32
<211> LENGTH: 32
<212> TYPE: PRT
<213> ORGANISM: Penicillium oxalicum
<220> FEATURE:
<223> OTHER INFORMATION: part of sequence from endoglucanase I

<400> SEQUENCE: 32

Trp Gly Gln Cys Gly Gly Gln Gly Tyr Thr Gly Pro Thr Ala Cys Val
1               5                   10                  15

Ser Gly Thr Thr Cys Lys Ala Gln Asn Pro Tyr Tyr Ser Gln Cys Leu
            20                  25                  30

<210> SEQ ID NO 33
<211> LENGTH: 32
<212> TYPE: PRT
<213> ORGANISM: Penicillium decumbens
<220> FEATURE:
<223> OTHER INFORMATION: part of sequence from endoglucanase I

<400> SEQUENCE: 33

Trp Gly Gln Cys Gly Gly Gln Gly Tyr Thr Gly Pro Thr Ala Cys Val
1               5                   10                  15

Ser Gly Thr Thr Cys Lys Ala Gln Asn Pro Tyr Tyr Ser Gln Cys Leu
            20                  25                  30

<210> SEQ ID NO 34
<211> LENGTH: 32
<212> TYPE: PRT
<213> ORGANISM: Talaromyces emersonii
<220> FEATURE:
<223> OTHER INFORMATION: part of sequence from cellulose binding protein

<400> SEQUENCE: 34

Trp Gly Gln Cys Gly Gly Leu Gly Trp Thr Gly Pro Thr Val Cys Ala
1               5                   10                  15

Ser Gly Phe Thr Cys Thr Val Ile Asn Glu Tyr Tyr Ser Gln Cys Leu
            20                  25                  30

<210> SEQ ID NO 35
<211> LENGTH: 32
<212> TYPE: PRT
<213> ORGANISM: Phanerochaete chrysosporium
<220> FEATURE:
```

-continued

<223> OTHER INFORMATION: part of sequence from cellulose-binding
      beta-glucosidase

<400> SEQUENCE: 35

Tyr Gln Gln Cys Gly Gly Ile Gly Trp Thr Gly Ala Thr Thr Cys Val
1               5                   10                  15

Ser Gly Ala Thr Cys Thr Val Leu Asn Pro Tyr Tyr Ser Gln Cys Leu
            20                  25                  30

<210> SEQ ID NO 36
<211> LENGTH: 34
<212> TYPE: PRT
<213> ORGANISM: Aspergillus fumigatus Af293
<220> FEATURE:
<223> OTHER INFORMATION: part of sequence from Acetyl xylan esterase

<400> SEQUENCE: 36

Glu His Trp Gly Gln Cys Gly Gly Asn Gly Trp Thr Gly Pro Thr Ala
1               5                   10                  15

Cys Ala Ser Gly Tyr Thr Cys Thr Val Ile Asn Glu Trp Tyr Ser Gln
            20                  25                  30

Cys Leu

<210> SEQ ID NO 37
<211> LENGTH: 36
<212> TYPE: PRT
<213> ORGANISM: Coprinopsis cinerea okayama7#130
<220> FEATURE:
<223> OTHER INFORMATION: part of sequence from glycosyl hydrolase family
      62 protein

<400> SEQUENCE: 37

Thr Ala Asp His Trp Ala Gln Cys Gly Gly Arg Gly Phe Ser Gly Pro
1               5                   10                  15

Thr Thr Cys Ala Ser Gly Ala Val Cys Thr Val Val Asn Glu Trp Tyr
            20                  25                  30

Ser Gln Cys Ile
        35

<210> SEQ ID NO 38
<211> LENGTH: 34
<212> TYPE: PRT
<213> ORGANISM: Phanerochaete chrysosporium
<220> FEATURE:
<223> OTHER INFORMATION: part of sequence from Family 61 endoglucanase

<400> SEQUENCE: 38

Ala Lys Tyr Gly Gln Cys Gly Gly Leu Thr Tyr Thr Gly Pro Thr Thr
1               5                   10                  15

Cys Val Ser Gly Thr Thr Cys Thr Ala Leu Asn Asp Tyr Tyr Ser Gln
            20                  25                  30

Cys Leu

<210> SEQ ID NO 39
<211> LENGTH: 35
<212> TYPE: PRT
<213> ORGANISM: Aspergillus clavatus NRRL 1
<220> FEATURE:
<223> OTHER INFORMATION: part of sequence from Fungal cellulose binding
      domain protein

<400> SEQUENCE: 39

Gln Ser Leu Tyr Gly Gln Cys Gly Gly Asn Gly Trp Ser Gly Pro Thr
1               5                   10                  15

```
Glu Cys Thr Ala Gly Ala Cys Cys Gln Val Gln Asn Pro Trp Tyr Ser
            20                  25                  30

Gln Cys Leu
        35

<210> SEQ ID NO 40
<211> LENGTH: 36
<212> TYPE: PRT
<213> ORGANISM: Lentinula edodes
<220> FEATURE:
<223> OTHER INFORMATION: part of sequence from cellulase CEL7A

<400> SEQUENCE: 40

Thr Gln Thr Lys Tyr Gly Gln Cys Gly Gly Gln Gly Trp Thr Gly Ala
1               5                   10                  15

Thr Val Cys Ala Ser Gly Ser Thr Cys Thr Ser Ser Gly Pro Tyr Tyr
            20                  25                  30

Ser Gln Cys Leu
        35

<210> SEQ ID NO 41
<211> LENGTH: 34
<212> TYPE: PRT
<213> ORGANISM: Verticillium albo-atrum VaMs.102
<220> FEATURE:
<223> OTHER INFORMATION: part of sequence from exoglucanase

<400> SEQUENCE: 41

Ser Gln Trp Gly Gln Cys Gly Gly Gln Gly Trp Ser Gly Pro Thr Cys
1               5                   10                  15

Cys Pro Ser Gly Thr Thr Cys Gln Leu Gln Asn Ala Trp Tyr Ser Gln
            20                  25                  30

Cys Leu

<210> SEQ ID NO 42
<211> LENGTH: 35
<212> TYPE: PRT
<213> ORGANISM: Acremonium cellulolyticus Y-94
<220> FEATURE:
<223> OTHER INFORMATION: part of sequence from cellobiohydrolase II

<400> SEQUENCE: 42

Gln Ser Val Trp Gly Gln Cys Gly Gly Gln Gly Trp Ser Gly Ala Thr
1               5                   10                  15

Ser Cys Ala Ala Gly Ser Thr Cys Ser Thr Leu Asn Pro Tyr Tyr Ala
            20                  25                  30

Gln Cys Ile
        35

<210> SEQ ID NO 43
<211> LENGTH: 33
<212> TYPE: PRT
<213> ORGANISM: Neosartorya fischeri NRRL 181
<220> FEATURE:
<223> OTHER INFORMATION: part of sequence from glycosyl hydrolase family
      7 protein

<400> SEQUENCE: 43

His Tyr Gly Gln Cys Gly Gly Asn Gly Trp Gln Gly Pro Thr Thr Cys
1               5                   10                  15

Ala Ser Pro Tyr Thr Cys Gln Lys Leu Asn Asp Phe Tyr Ser Gln Cys
            20                  25                  30
```

-continued

Leu

<210> SEQ ID NO 44
<211> LENGTH: 32
<212> TYPE: PRT
<213> ORGANISM: Lentinula edodes
<220> FEATURE:
<223> OTHER INFORMATION: part of sequence from cellulase CEL6B

<400> SEQUENCE: 44

Tyr Gly Gln Cys Gly Gly Ile Gly Trp Ser Gly Ala Thr Thr Cys Val
1               5                   10                  15

Ser Gly Ala Thr Cys Thr Val Val Asn Ala Tyr Tyr Ser Gln Cys Leu
            20                  25                  30